United States Patent [19]

Choperena et al.

[11] Patent Number: 5,693,292

[45] Date of Patent: Dec. 2, 1997

[54] DEVICE FOR AUTOMATIC CHEMICAL ANALYSIS

[75] Inventors: Alfredo Choperena, Eden Prairie; Ross Krogh, Minneapolis; Venkatesh Prasad, Eden Prairie; Gershon Giter, St. Paul, all of Minn.

[73] Assignee: Pasteur Sanofi Diagnostics, France

[21] Appl. No.: 477,813

[22] Filed: Jun. 7, 1995

Related U.S. Application Data

[62] Division of Ser. No. 370,910, Jan. 10, 1995, which is a continuation of Ser. No. 878,956, May 5, 1992, Pat. No. 5,380,487.

[51] Int. Cl.⁶ .................................................. G01N 35/04
[52] U.S. Cl. .......................... 422/67; 422/63; 422/64; 422/65; 436/43; 436/47; 436/48; 436/49; 436/50
[58] Field of Search .................... 422/63–67, 100, 422/104; 436/43, 47, 48, 49, 50, 55, 180; 364/497, 500

[56] References Cited

U.S. PATENT DOCUMENTS

| | | |
|---|---|---|
| 3,644,095 | 2/1972 | Netheler et al. . |
| 3,775,909 | 12/1973 | Best et al. . |
| 4,058,367 | 11/1977 | Gilford . |
| 4,098,305 | 7/1978 | Gates . |
| 4,281,387 | 7/1981 | Kraft et al. . |
| 4,287,155 | 9/1981 | Tersteeg et al. . |
| 4,311,394 | 1/1982 | Manabe . |
| 4,427,294 | 1/1984 | Nardo . |
| 4,456,037 | 6/1984 | Gocho . |

(List continued on next page.)

FOREIGN PATENT DOCUMENTS

| | | |
|---|---|---|
| 0355823 | 2/1990 | European Pat. Off. . |
| 0358948 | 3/1990 | European Pat. Off. . |
| 0487149 | 5/1992 | European Pat. Off. . |
| 2280894 | 2/1976 | France . |
| 2519111 | 7/1976 | Germany . |
| 2855088 | 7/1980 | Germany . |
| 3934890 | 4/1990 | Germany . |
| 535073 | 3/1973 | Switzerland . |
| 9001168 | 2/1990 | WIPO . |
| 9205448 | 4/1992 | WIPO . |
| 9303347 | 2/1993 | WIPO . |
| 9322686 | 11/1993 | WIPO . |

OTHER PUBLICATIONS

*Journal of Clinical Immunoassay*, vol. 14, No. 2, Summer 1991 (pp. 77–136).
Brochure entitled "Now Because Time is of the Essence, SR1 Provides Immediate Access for Timely Results," Serono–Baker Diagnostics.
Field, et al., "Overlapped Processing in Wet Chemical Analyzer", IBM Technical Disclosure Bulletin, vol. 19, No. 3, Aug. 1976, pp. 1022–1024.

*Primary Examiner*—Long V. Le
*Attorney, Agent, or Firm*—Fredrikson & Byron, PA

[57] ABSTRACT

This invention provides an automated chemical analyzer with improved processing flexibility and ease. In one embodiment of this invention, the analyzer includes an incubation station, a wash station and a read station. The incubation station includes an elongated, movable track to carry reaction vessels along an incubation path, the wash station includes a movable track to carry vessels along a wash-cycle path, and the read station is adapted to move vessels along a read path. A first transfer station is positioned adjacent a first end of the wash-cycle path to transfer vessels from the incubation path to the wash-cycle path and a second transfer station is positioned adjacent a second end of the wash-cycle path and a first end of the read path for selectively transferring a vessel from the wash-cycle path to either the incubation path or the read path. The system also includes an analyzer controller having scheduling means for allocating assay resources to one of the reaction vessels and transfer control means for controlling the transfer of reaction vessels from one assay resource station to another according to a chronology selected from a plurality of different predetermined chronologies.

20 Claims, 13 Drawing Sheets

U.S. PATENT DOCUMENTS

| | | |
|---|---|---|
| 4,647,432 | 3/1987 | Wakatake . |
| 4,678,752 | 7/1987 | Thorne et al. . |
| 4,689,202 | 8/1987 | Khoja et al. . |
| 4,849,176 | 7/1989 | Sakagami . |
| 4,857,471 | 8/1989 | Salzman et al. . |
| 4,906,433 | 3/1990 | Minekane . |
| 4,908,320 | 3/1990 | Zakowski et al. . |
| 5,087,423 | 2/1992 | Ishibashi . |
| 5,102,624 | 4/1992 | Muraishi . |
| 5,104,808 | 4/1992 | Laska et al. . |
| 5,244,633 | 9/1993 | Jakubowicz et al. . |
| 5,282,149 | 1/1994 | Grandone et al. . |
| 5,316,726 | 5/1994 | Babson et al. . |
| 5,380,487 | 1/1995 | Choperena et al. . |

Fig. 11

| INDEXING CYCLE | PROBE ACCESS | ENTER WASH WHEEL | ENTER READ STATION |
|---|---|---|---|
| 0 | 1 | | |
| 1 | 2 | | |
| 2 | 3 | | |
| 3 | 4 | | |
| 4 | 5 | | |
| 5 | | 1 | |
| 6 | | 2 | |
| 7 | | | |
| 8 | 6 | | |
| 9 | | | |
| 10 | 1 | 3 | |
| 11 | 2 | 4 | |
| 12 | | 5 | |
| 13 | | 6 | |
| 14 | | | — |
| 15 | | 1 | 3 |
| 16 | | 2 | 4 |
| 17 | | | 5 |
| 18 | 6 | | |
| 19 | | | |
| 20 | | | 1 |
| 21 | | | 2 |
| 22 | | | |
| 23 | | 6 | |
| 24 | | | |
| 25 | | | |
| 26 | | | |
| 27 | | | |
| 28 | | | 6 |
| 29 | | | |
| 30 | | | |

DEVICE FOR AUTOMATIC CHEMICAL ANALYSIS

This is a divisional of application Ser. No. 08/370,910, filed Jan. 10, 1995, which is a continuation of Ser. No. 07/878,956 filed May 5, 1992 (now U.S. Pat. No. 5,380,487).

FIELD OF THE INVENTION

The present invention relates to automated chemical analysis methods and apparatuses, such as are used in the field of diagnostics. In particular, the present invention provides an apparatus and method for efficiently scheduling and performing analytical tests on samples.

BACKGROUND OF THE INVENTION

Automated chemical analyzers have proved to be useful tools in clinical laboratory settings. Quantitative chemical analysis requires precise control of such factors as time of reaction, temperature and reagent concentration. Tests manually conducted typically lack precise control of these parameters resulting in inaccurate or irreproducible results. Additionally, manual testing limits the speed of processing, makes the handling of large numbers of samples difficult and introduces the possibility of human error, such as misidentification of samples.

Fully automated chemical analyzers automatically obtain a volume of a patient sample suspected of containing a particular analyte, add reagents to the sample and control reaction parameters such as time and temperature. Such analyzers usually include a transport or conveyor system designed to transport containers of reaction mixtures of sample and reagents to various operating stations. Reactions between analyte in the sample and reagents result in a detectable signal automatically measurable by the instrument. The measured value is then compared to a calibration curve that is generally stored in the instrument, to determine the final test result: the concentration of the analyte in the patient sample.

A number of automated chemical analyzers are currently available on the market. These analyzers differ somewhat in the methods by which the samples and reaction mixtures are processed once they are introduced to the analyzer by the operator. Volume 14 of the *Journal of Clinical Immunoassay*, Summer 1991, ("J. Clin. Immun."), the teachings of which are incorporated herein by reference, provides a description of several of such automated analyzers.

Known analyzers differ in the frequency at which new samples or tests can be introduced to the analyzer for analysis. In an instrument with "batch access", a plurality of samples is introduced to the analyzer in a set and a new set of samples can be introduced to the analyzer only when analysis of all the samples in a prior set of samples is completed. In an instrument that has "continuous access," new samples may be introduced to the analyzer at any time, even when the analyzer is already in a running mode. In the clinical laboratory, it is sometimes necessary for an assay to be run immediately on a particular patient's sample. Such assays are referred to as STAT assays.

Examples of instruments that have batch access include the IMx Select System, manufactured by Abbott Laboratories, and the ES 300 Immunoassay System, manufactured by Boehringer Mannheim. in use, containers with sample liquids are placed on the transport circuit of these instruments in batches, and the containers travel in a fixed cycle so that each container passes through various operating stations in sequential order. In these instruments, all the sample containers must be processed before new samples are added. Some batch systems have means for assaying new samples on a STAT basis. In such systems, however, STAT sample introduction and processing are delayed until all the samples already in the assay process are completed.

Instruments that have continuous access of samples, as defined herein, include the IMMULITE™ Automated Immunoassay System manufactured by Cirrus, the Affinity™ Immunoassay System, manufactured by Becton Dickinson, the AIA-1200/AIS-600 Automated Immunoassay Analyzers, manufactured by TOSOH, the Immuno 1 Automated Immunoassay System, manufactured by Technicon, the System 7000 manufactured by Biotrol, and the OPUS™ mmunoassay System, manufactured by PB Diagnostics.

Another feature that differs among the automated analyzers currently available is the capability of the system to analyze one sample for multiple analytes during any period of operation. Analyzers that can analyze samples for two or more analytes, with two analysis methods being performed by the instrument simultaneously, will be described herein as having an "integrated mode of operation." Most of the automated analyzers currently available include this feature although the method in which the assays for multiple analytes are accomplished differs significantly.

In the diagnostics industry, the term "random access" is sometimes used to refer to the ability of an instrument to assay for any analyte on any sample at any time. It is desirable for all tests required on a sample to be done on one instrument at one time. Many of the instruments that have an integrated mode of operation purport to be "random access" instruments even though tests for certain analytes cannot be performed on some of the instruments because of limitations of the instrument's mode of operation.

Analyzers that have an integrated mode of operation can be further divided into subcategories based upon the flexibility of the instrument in handling the assay format requirements of various analytes. Some instruments deal with all tests using the same basic protocol. The amounts and type of reagents mixed with the sample may vary when testing for various analytes, but the reaction incubation time or the processing sequence is fixed. In some single protocol analyzers the incubation time for assay formats varies but only in multiples of the predetermined incubation length.

The IMMULITE™ Automated Immunoassay System is an example of an instrument having an integrated mode of operation but using a single protocol, although the incubation time for some analytes may be doubled.

Such single protocol instruments may assay for a broad menu of analytes but typically the lack of flexibility in assay protocols available results in decreased throughput or in decreased sensitivity for certain analytes.

Other automated analyzers with integrated modes of operation have a greater variation in assay protocol in terms of variations in incubation time, and perhaps in wash steps, than the single protocol instruments described above. For purposes of this description, such analyzers will be referred to as "multiple protocol" analyzers.

Typically, in multiple protocol analyzers the sequence of protocol steps varies. For example, one assay protocol may require sample exposure to an assay constituent pipetting station, followed by an incubation step and then detection of a labeled reagent at a reading station. Another assay protocol may require sample exposure to a reagent pipetting station, followed by an incubation step, followed by a second exposure to the reagent pipetting station, a second incubation and finally detection of a labeled reagent at a reading station. In this type of instrument, which is referred to herein as a "multiple chronology" instrument, the two assay protocols can be simultaneously processed.

The Affinity™ immunoassay System is one example of an instrument which is both multiple protocol and has multiple chronology processing. U.S. Pat. No. 4,678,752 describes the operational methods upon which this instrument is based in detail. The Affinity™ Immunoassay System includes means for transporting reagent packs in any order and in any direction as dictated by the assay protocol for a particular analyte.

Another feature which differs among known automated analyzers is the method used to schedule the timing Of the assay resources of the instrument. The assay resources include sample pipetting, reagent pipetting, incubator transfer stations, wash stations, read stations and the like. In any automated analyzer, some means must control the transport of assay constituents, i.e., reagents and sample, from one operational station to the next and also control the timing of the operations performed at such stations. The scheduling of such timing is typically controlled by a computer program.

One common method of scheduling assay resources is based upon the use of a predetermined fixed cycle. As used herein, "predetermined fixed cycle" shall mean any method of scheduling the timing of assay resources so that all the assay resources in the instrument operate within a fixed length, predetermined cycle. Systems having this scheduling method will have each assay resource returning to a predetermined location at the end of each cycle.

Known automated analyzers which have the predetermined fixed cycle method of scheduling the timing of resources also have single chronology operation. For example, both the IMMULITE™ Automated Immunoassay System and the ACS:180™ Automated Immunoassay System described have a predetermined fixed cycle method of scheduling resources. As described above, each container of sample proceeds through each of the operational stations of the above analyzer in the same order. The Dade Stratus II Immunoassay System is another such automated immunoassay system and is also described in Volume 14 of the J. Clin. Immun. In the Stratus analyzer reaction tabs are positioned around a generally circular wheel, with reaction tabs being disposed about the periphery of the wheel. An incubation stage, a washing stage and a reading stage are positioned around the periphery of the wheel. The wheel moves forward a fixed distance for each cycle of the system, indexing sequentially in a clockwise fashion past these stages.

In a normal, single stage assay, the sample and the necessary reagents are added at a pipetting location and the wheel begins to index forward through the incubation stage. Since the wheel indexes a fixed distance for each cycle of fixed duration, the incubation time for the sample is predetermined for all samples. The reaction vessel then moves on to the wash and read stages according to a fixed time schedule and the spent reaction vessel is discarded.

If a particular assay protocol requires a longer incubation time, the only option is to allow the sample to proceed through the wash and read stations and proceed back to the pipetting location without being discarded. This sample must then make the entire trip back around the wheel before it can be read. Not only does this significantly limit the flexibility of the system, it also requires assay resources (i.e., the wash and read stations and the pipetting location) to be dedicated to the sample even though the sample does not require these resources to perform any function.

As discussed above some assay formats, require two stages of processing, each stage requiring the addition of reagents, incubation and washing, and only after the second stage does the sample proceed to a reading step. In the known analyzers with predetermined fixed cycle methods of control, the assay constituents are transported in a vessel that cannot reverse direction and allow additional reagents, incubation, and washing steps to be performed before reading occurs. Automated analyzers with predetermined fixed cycle scheduling control currently available do not permit flexibility in incubation times between assay formats. Although assay protocols may vary for each analyte, all incubation times are generally the same. When the incubation time does differ, it is always a longer incubation time and it is a multiple of the "normal" incubation time for that analyzer. For example, in the ACS:180™ Automated Immunoassay System, the incubation time is doubled for certain analytes. This feature limits the availability of assay protocols on the analyzers.

Another type of scheduling method used in automated analyzers does not use a fixed cycle. This type of scheduling method will be referred to as "adaptive timing." Adaptive timing, as used herein, means that the assay resources are scheduled and controlled in such a way that the timing may vary depending on the status of the analysis in process. For instance, the timing may vary based on a measured reaction parameter, e.g. reaching a predetermined threshold level or a predetermined signal rate.

Known automated analyzers that have a multiple protocol, multiple chronology processing format all have adaptive timing control of the assay resources. As described above, such analyzers differ from the single chronology processing, predetermined fixed cycle analyzers in that their operation is much less rigidly time-dependent. In adaptive timing analyzers, the timing of the addition of various reagents, the incubation time, and other time-dependent functions can be varied individually for each assay. This greatly enhances the flexibility of such analyzers. However, the information that must be accurately recorded and tracked for each individual assay handled by the analyzer greatly increases the complexity of the control. The more assays being processed in such an analyzer at any give time, the greater the difficulties will be in accurately controlling the system to conduct the test. Additionally, every test performed on the analyzer will require its own specific reagents and processing times. By adding wider test capabilities, the amount of information that must be handled by the analyzer controller becomes that much more complex. The complexity of the control in such adaptive timing analyzers can significantly affect the throughput of the system—as the complexity of the control system increases, the number of samples that the analyzer can process in a given time decreases. Moreover, as the number of assay resources required for a particular protocol increases, the complexity of control in an adaptive timing controlled analyzer increases.

Automated analyzers such as the Affinity™ Immunoassay System have adaptive timing and use a complex scheduler program to handle the multiple protocols. As described in U.S. Pat. No. 4,678,752, the scheduler program of the instrument claimed therein examines all of the actions required to complete the processing of the samples currently in the apparatus, and then arranges them into a sequence which attempts to use the capabilities of the apparatus efficiently. First, the scheduler determines whether any samples have been introduced to the analyzer, the processing of which must be scheduled. The scheduler prioritizes the processing of reagent packages with those samples, a schedule plan is made and a scheduling order is arranged. Each new sample added to the analyzer has its own schedule plan that is then fit into the scheduling order.

It would be desirable to have an automated chemical analyzer that had the multiple protocol, multiple chronology processing and the flexibility provided thereby with the simplicity of the predetermined fixed length cycle method of scheduling the assay resources.

SUMMARY OF THE INVENTION

The present invention provides methods and apparatuses that permit the clinical analysis of samples for multiple analytes with a variety of assay protocols in a multiple chronology sequence while operating on a predetermined fixed length cycle method of timing control. This method provides unique flexibility and mechanical and control simplicity.

In one method of the invention, analyzer control means are provided comprising scheduling means and transfer control means. A fixed cycle length is predetermined for controlling certain assay resources located in assay resource stations and that information is provided to the scheduling means. These assay resources are generally an assay constituent delivery means, an incubator belt, a wash means and signal detection means. Each of the assay resources is assigned a fixed operating sequence, that is a time period of fixed duration during which that assay resource is available to perform a predetermined operation on a sample-containing reaction vessel, that begins and ends within the time cycle of predetermined length. Desirably, an operating sequence that is a first indexing cycle having a first indexing time is assigned to one of the assay resources, such as the incubator. In a preferred embodiment, that first indexing time equals the fixed cycle length predetermined for controlling the scheduling of assays. Each of the other assay resources is also assigned a fixed operating sequence, where the first indexing time is preferably an integral multiple of each such operating sequence so that the incubator and the other assay resources operate synchronously with each other. Although the integral multiple may be one, such that the first indexing time may be equal to the fixed sequence of the other assay resources, the two cycle times desirably differ from one another. In a preferred embodiment, the integral multiple is three, i.e., the first indexing time of the incubation belt is three times as long as the operating sequence time of the other assay resources.

As noted above, known automatic analyzers that can process multiple protocols using multiple chronology have very complex methods of controlling the processing. A precise schedule for each and every sample and reaction vessel must be stored and the controller must ensure that a specific assay resource, such as a dispensing pipette, is available at the precise time it is required.

In the method of this invention, each assay resource has a predetermined fixed operation window within the fixed processing cycle. Resultingly, the control logic for one assay resource can rely on predetermined timing of other dependent and independent assay resources. Therefore, analyte tests having variable protocols and that are processed by moving reaction vessels in different chronologies can be interleaved if their assay resource requirements do not conflict, i.e., analyte tests with shorter processing time can be entered after those with longer processing times and the shorter analyte test can finish first. This can be done because the means of transporting reaction vessels containing assay constituents can present reaction vessels to the necessary assay resources in whatever order is required, regardless of entry order. In a preferred embodiment an optimizing routine is used by the analyzer control means for increased performance and throughput.

In an embodiment of the invention, variable dwell time in an assay resource station may be achieved for the various analyte test protocols by using independent internal storage or by providing the reaction vessel transport means with excess capacity.

The method of the present invention greatly simplifies scheduling while maintaining a maximum degree of flexibility in the system. Whereas known multiple protocol, multiple chronology analyzers operate on a true time line in a fashion analogous to analog electrical processing, the method of the present invention schedules in terms of discrete time slots, more like digital processing of electrical signals. Each time slot of the analyzer as a whole is desirably equal to the first indexing time of the incubator belt. Thus, a reaction vessel can be transferred to the wash wheel only at the beginning of the indexing cycle of the incubator. Because the a processing cycle is fixed, the indexing cycle of the incubator in the preferred embodiment, and the scheduling means matches analyte tests and assay resources within such a cycle, greatly simplifying the scheduling.

Process control is also simpler in the method of the invention. In adaptive timing analyzers, a resource must constantly monitor the status of other dependent resources to determine the subsequent timing of its actions. Analyzers controlled as described herein have time cycles of fixed duration that can be relied upon by the scheduling means in ensuring each assay resource will complete its operations within the predetermined time without constantly polling the status of other resources.

Interleaving of analyte tests with different protocols is not possible with known adaptive timing analyzers. Such analyzers control means must follow a first-in-first-out pattern of entering and processing the test, and an interruption of entry of a test results in a "hole" that consumes assay resources and increases the overall time required to process a worklist. In the method of the invention, the ability to interleave analyte tests makes it possible for the "hole" to be filled with another analyte test having compatible assay resource requirements. The result is shorter overall processing times for interrupted worklists or for systems that receive intermittent analyte test entry.

In the analyzer of the invention, the dwell time of a reaction vessel containing assay constituents on the incubator belt is limited to a time approximately equal to an integral multiple of that first indexing time. In actuality, the actual time a vessel spends on the incubator belt may be slightly less than a full integral multiple of the first indexing time because it takes a short period of time after a reaction vessel is transferred to the wash wheel at the first wash transfer station before the incubator moves to the incubator transfer station to add a new vessel to the incubator. The use of a fixed cycle of predetermined length limits the "chronological resolution" (i.e., the accuracy with which a given time can be varied) that may achieved in controlling the dwell time of a vessel in the incubator. Specifically, the analyte test must be based on a protocol where the incubation time will fall within a range of incubation times within one half the first indexing time. (For example, if the first indexing time is 36 seconds, the incubation times of the protocols would be variable within ±18 sec). This slight variability in incubation time does not, however, result in loss of precision, thus ensuring that the test results are reproducible.

In use, an apparatus of the invention transports reaction vessels containing the assay constituents for a particular analyte test to the various assay resource stations where assay resources associated with the station are capable of performing one or more predetermined operations on the reaction vessels during the fixed time slot of availability assigned to such assay resource. For example, the assay constituent delivery means delivers predetermined amounts of sample and reagents to the vessel. The incubator belt may transfer a reaction vessel along a predetermined path in the incubator. In the wash station, assay resources act upon the reaction vessel by transporting the vessel to one or more positions in the apparatus, where labeled reagents bound to a solid phase are separated from unbound labeled reagents and buffer is dispensed and aspirated from the reaction vessel. In the read station, assay resources act upon a reaction vessel by transporting the vessel first to a position in the apparatus where reagents required to provide a detectable signal will be added and then to a signal detection means, a luminometer in the preferred embodiment of this invention, where signal is detected and recorded by the apparatus.

One embodiment of an apparatus of this invention includes the following predetermined assay resources: assay constituent delivery means, an incubator belt, separation and wash means and means for detecting a signal. The apparatus will also include means for transporting a reaction vessel from one resource to another and analyzer control means described above. A particularly preferred embodiment includes as an assay resource a vessel chain positioned in the apparatus so that assay constituents may be added to a reaction vessel while the vessel is on the vessel chain before the vessel is transferred to another assay resource so that transport of other reaction vessels is not delayed during the delivery process.

The wash station is preferably physically integrated with the read station along a continuous, endless path on a wash wheel. This physical integration of the two stations, combined with the mechanical simplicity of the transfer stations, reduces the mechanical complexity of the analyzer of the invention over other analyzers known in the art; such systems generally require complex transfer mechanisms having separate motors and the like for transferring vessels from one stage of processing to another or the vessels follow only a single path and must proceed sequentially through each operational station. Mechanical simplicity increases the reliability of the analyzer of the invention by reducing the number and complexity of moving parts in the analyzer. Another advantage provided by the physical integration of the read and wash station is that the entire analyzer can be very compact. In a preferred embodiment, the wash wheel, incubator belt and assay constituent supply wheel are all arranged with respect to each other and with respect to the electronics and fluidics of the analyzer so that every assay resource can be accessed by an operator from a single stationary position in front of the analyzer.

Even though the wash and read stations are physically integrated, they are logically separate, i.e., separately controllable by the analyzer control means.

BRIEF DESCRIPTION OF THE DRAWINGS

FIG. 11 is a schematic representation of a time-dependent assay resource availability schedule for a series of assays performed on an analyzer of the invention.

DETAILED DESCRIPTION OF THE PREFERRED EMBODIMENTS

Figure 1:
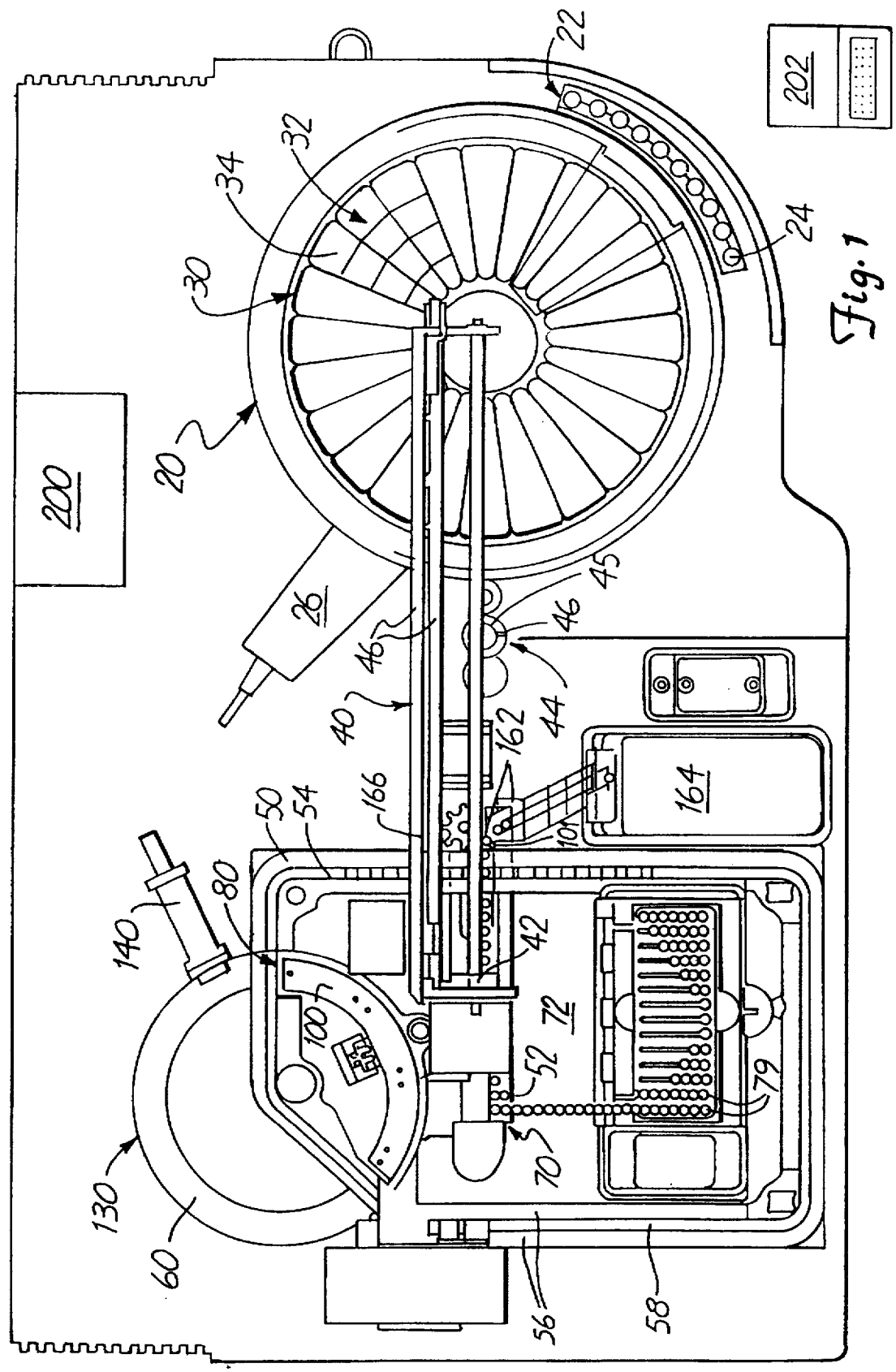
FIG. 1 is a schematic representation of an analyzer of the invention.

FIG. 1 schematically represents an analyzer 10 of the invention. The analyzer shown includes an assay constituents supply wheel 20, an assay constituents delivery means 40, an incubator 50, a wash wheel 60 positioned adjacent a wash station 100 and a read station 130 and various other components that will be described below.

The assay constituents supply wheel 20 rotates in a generally horizontal plane and includes an annular outer carousel 22 for receiving a series of samples, samples may be patient specimens, controls or calibrators, and an inner carousel 30 for storing a plurality of reagent packs 32. Each sample is preferably provided in a sample cup 24 adapted to be safely and securely received on the outer carousel 22. A plurality of these sample cups is provided on this annular carousel so that a sample may be placed in the analyzer at the operator's convenience.

Although FIG. 1 depicts the outer carousel 22 as comprising only a relatively short arc, the outer carousel preferably extends about the entire periphery of the supply wheel 20. In one preferred embodiment, sample cup container trays may be included which are designed in a short arc and which are adapted to fit on the outer carousel of the supply wheel. The container trays desirably are designed to receive a plurality of sample cups and a plurality of these trays may be positioned about the periphery of the supply wheel. In a preferred embodiment, these trays are independently removable, permitting batches of sample cups to be swapped out of the analyzer in a single step. The sample trays are desirably designed to support use of containers of a variety of shapes. For example, the sample tray of the analyzer shown will support sample cups designed for the tray, 13×75 mm or 13×100 mm test tubes, and 13×75 mm or 13/100 mm serum separator test tubes.

Once the operator has placed patient sample in a sample cup on the analyzer, the operator must provide analyzer control means with information identifying the sample and the analyte test to be performed on the sample. This information must include the position of the sample cup on the apparatus. The operator may manually enter the identifying information about a sample or the information may be provided on the sample cup with a label readable by the analyzer, such as a bar code label. A bar code reader 26 may be included in the analyzer for this purpose.

Reagent packs 32 are designed to be positioned on the inner carousel 30 of the supply wheel. Each pack desirably includes a plurality of discrete wells 34 in which a quantity of a given reagent may be stored. Preferably, each reagent pack is analyte-specific and provides a sufficient quantity of each reagent necessary to process at least one analyte test. The packs desirably include a sufficient quantity of each reagent to conduct a number of analyte tests on different patient samples. When the reagents in a pack are exhausted the operator removes the pack and replaces it with a new one. The inner carousel 30 of the assay constituents supply wheel may be refrigerated to maintain reagents stored in the apparatus at refrigeration temperatures, 4°–10° C., increasing reagent shelf-life and stability. Information regarding the position and contents of each reagent pack 34 may be provided to the analyzer control means using a label readable by the analyzer. Such information may include reagent pack test name, lot number, expiration date and the like. As with the sample cups, the label is preferably a bar code label that may be read by a reader included in the apparatus or by a wand type bar code reader. The information on the label may also be entered manually.

The analyzer shown in FIG. 1 begins processing an analyte by using assay constituents delivery means 40 to withdraw a predetermined amount of patient sample from a sample cup and transfer it to a reaction vessel held elsewhere in the apparatus. In a preferred embodiment, the delivery means includes a probe 42 that has an ultrasonically activatable tip (not shown) and a pump (not shown). Ultrasonic vibrations generated by an ultrasonic transducer may be applied to the probe tip to mix fluids in the reaction vessel, sample cup or reagent pack wells before or after aspiration, to clean the probe after each use, and for liquid level sensing. Assay constituents delivery means useful in automated analyzers and ultrasonic probes are well known and will not be described in detail here. The probe may include means for heating the liquid it withdraws from a vessel. This feature allows the liquid to be preheated to the incubation temperature before it is dispensed into a reaction vessel. In a preferred embodiment the pump is a dual-resolution diluter pump, such as the pump described in U.S. Pat. No. 4,941,808. This pump permits accurate and precise delivery of both large and small fluid volumes. The pump delivers wash buffer to the prove for washing and sample dilutions. It also aspirates samples and reagents into the probe for delivery into reaction vessels.

As indicated schematically in FIG. 1, the assay constituents delivery means 40 is adapted to access a sample cup 24 containing a patient sample, a reaction vessel 52 and each of the wells 34 of a selected reagent pack. In FIG. 1, the assay constituents delivery means is represented as a single probe 42. If desired, a plurality of probes may be employed, e.g., with one probe dedicated to transferring patient sample and one or more probes used to transfer reagents.

In the analyzer shown in FIG. 1, the probe 42 is carried on a track 46. This permits the probe to move laterally from an aspirating position over a sample cup or a reagent well to a dispensing position (as shown), where the aspirated liquids may be dispensed into a reaction vessel. The inner and outer carousels (30 and 22, respectively) of the supply wheel are independently rotatable about their axis so that any desired patient sample and any desired reagent pack can be independently positioned for access.

In a preferred embodiment, the reagent packs are covered with a resealable material that may be pierced by the probe tip but which will substantially reseal as the tip is withdrawn.

Once a predetermined amount of patient sample is dispensed into a reaction vessel, the reagent or reagents necessary for the specified test are added to the reaction vessel.

In a preferred embodiment, magnetic or paramagnetic particles are used as a solid support. Alternatively, of course, beads or the tube walls may be coated and used as a solid support utilizing known procedures. When the magnetic particles are used, each reagent pack 32 contains magnetic particles which may be coated with an assay-specific reagent or which may be coated with a generic reagent. The particles are stored in the reagent pack in a buffer solution. Desirably, before the predetermined amount of buffer-particle solution is withdrawn from the reagent pack, the solution is mixed by some means. In one embodiment, the ultrasonic probe is vibrated to mix the fluid to uniformly suspend the particles. Alternatively, the apparatus could include means for vortexing the liquid in the well or means for stirring the liquid using a stirring bar.

The analyzer shown in FIG. 1 includes a probe washing station 44. In order to avoid cross-contamination between patient samples or between patient samples and reagent supplies, after the probe of the assay constituents delivery means has dispensed a quantity of liquid, it should be cleansed. In the preferred analyzer, the probe washing station 44 includes a toroidal fluid delivery band 45 carried on the inner walls of a drain cup 46 positioned beneath the band 45. The fluid delivery band 45 is arranged to be coaxial with the probe tip and the probe tip may be inserted through the band. The fluid delivery band comprises a tubular component having ports spaced circumferentially about the band surface that face generally radially inwardly toward the probe tip. The band should be of a sufficient diameter so that when the probe tip is inserted, the outer surfaces of the probe do not touch the walls of the band. The band diameter should, however, be small enough so that fluid may flow through the ports and wet the outer probe surface to cleanse it. The inner probe surface is desirably cleansed by flowing a quantity of a wash or cleansing solution through it. The drain cup 46 is arranged to receive probe cleansing solution and conduct that fluid to a waste container (not shown).

In a preferred analyzer the probe washing station further includes drying means that draws air and cleaning solution through the band into the drain cup and about the outer surface of the probe to pull excess liquid from the probe surface. When a ultrasonic probe is used, the probe is desirably ultrasonically activated for a sufficient period of time to atomize fluid on the surface of the probe, to aid in drying the probe.

During the sample and reagent dispensing steps, the reaction vessel may be positioned on the incubator belt 54 of the incubator 50. In such an embodiment, however, the incubator belt would have to remain essentially stationary during the liquid dispensing cycle, thus delaying the transport of other reaction vessels by the incubator belt. To avoid this delay, a preferred embodiment of the analyzer includes an assay constituent dispensing station 55 (FIG. 2) that includes a vessel chain 70 positioned off the incubator belt 54. The vessel chain 70 is desirably adapted to carry a plurality of vessels along its length. The vessel chain 70 desirably includes a floor 73 for supporting the bottom of a reaction vessel, a series of parallel, spaced-apart fingers 71 for supporting diametrically opposed sides of the vessel and parallel means for supporting the other opposing sides of the vessel to hold the vessel in a generally vertical position. The parallel means may include a supporting wall 74 on one side and an empty vessel from the new vessel loader 72 (FIG. 1) on the other side. The new vessel loader 72 is provided adjacent the vessel chain 70 to supply new reaction vessels to the analyzer. The new vessel loader is readily accessible to an operator to permit the operator to add additional reaction vessels to the supply as the analyzer disposes of used reaction vessels.

The new vessel loader 72 desirably presents a series of essentially parallel lines of new vessel to the chain 70, with the lines being spaced to position a new vessel in each line immediately adjacent a vessel carrying position on the vessel chain. The new vessel loader shown includes a series of parallel supporting walls 79 spaced to allow a vessel to slide between them while supporting the vessel in a generally vertical position. Each row of empty vessels is urged forward by a substantially vertical finger (not shown) that is slidably mounted in the floor of each row and supports the outermost (i.e., closest to the bottom in FIG. 1) empty vessel of each row. In the event no empty vessels are present in a row of the new vessel loader, the vertical finger will support a reaction vessel on the vessel chain 70.

Figure 2:
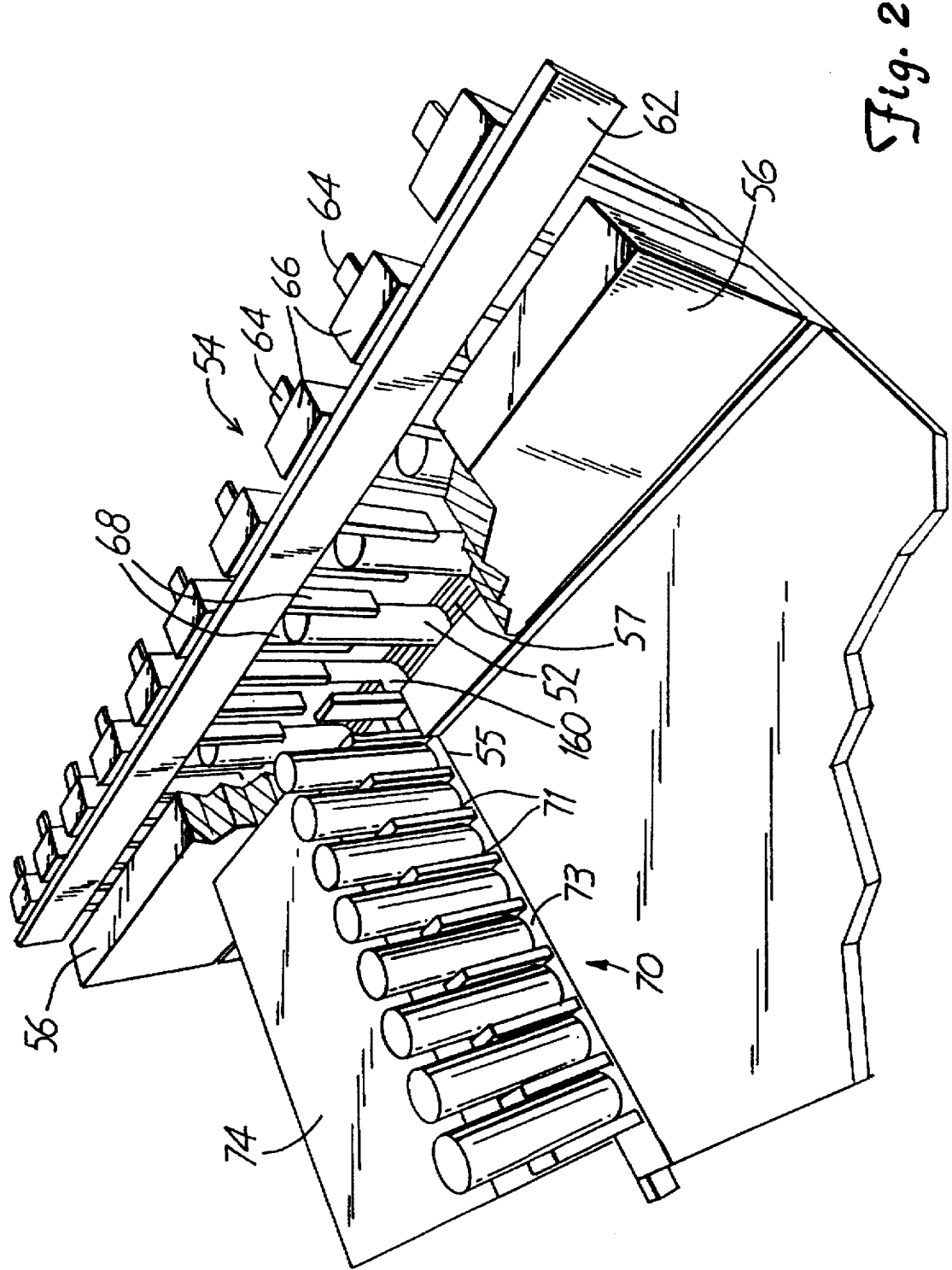
FIG. 2 is a perspective isolation view of a portion of the analyzer of FIG. 1 showing a portion of the vessel chain and a portion of the incubator belt and the interaction therebetween.

In the embodiment shown in FIGS. 1 and 2, the vessel chain intersects the incubator belt 54 at the incubation transfer station 160 and continues to a vessel disposal station 162. At the incubation transfer station 160 the reaction vessel may be transferred to or from the incubator belt or it may be transported to the vessel disposal station. In a preferred embodiment, the vessel accessed by the probe 42 during any operating cycle of the analyzer is spaced two positions away from the incubation transfer station. When all the necessary fluids have been added to that vessel, the vessel chain will be moved forward (to the right in FIG. 1) two positions, positioning that vessel at the incubation transfer station. After the vessel is removed from the vessel chain, as described in detail below, the vessel chain will be retracted (to the left in FIG. 1), placing a new vessel in position for access by the probe. In most analyses, the vessel chain will be retracted only one position.

Some assay protocols require "two-stage" processing, where additional reagents must be added to a reaction vessel after a first incubation and washing process. When a reaction vessel requires such additional reagent addition steps, the vessel chain may be retracted two positions, rather than one. First, sample and reagents are added to an empty reaction vessel, that reaction vessel is moved forward two positions to the incubation transfer station 160, and that vessel is transferred onto the incubator belt. Before the vessel chain retracts, the reaction vessel requiring additional reagent is positioned at the incubation transfer station. The chain is retracted two positions, transferring the vessel to the chain and positioning it at the probe's dispensing position. After additional reagent has been added to that reaction vessel, the vessel chains moves the vessel forward two positions back to the incubation transfer station for transfer onto the belt.

When all the new vessels on the chain are used, the chain is positioned adjacent the vessel supply and all of the lines of vessels in the new vessel loader 72 will be indexed forward one position by urging the vessels in line forward about the width of one vessel. This will add one new vessel to the chain from each line of vessels, providing a series of new vessels on the chain for use. Once those vessels have been used, the process may be repeated.

The vessel chain may be of any useful configuration, and the incubation transfer station may be of any type. In a preferred embodiment, however, vessels will transfer from the vessel chain to the incubator belt in the same manner in which vessels are transferred to and from the wash wheel which is described in detail below.

The incubator 50 desirably has an incubator belt 54 which is designed to transport one or more reaction vessels in any direction along a predetermined path 58. Although the schematic depiction of FIG. 1 shows reaction vessels only along a portion of the circumference of the incubator, the incubator desirably is adapted to carry vessels along its entire circumference. The reaction vessels are adapted for movement together within the incubator, but they should be relatively easily placed onto or removed from the belt. In one preferred embodiment described below in connection with FIGS. 3–9, the belt 54 is adapted to releasably receive and engage each of the vessels for movement therewith.

The incubator desirably includes a housing which includes a pair of parallel walls 56 which are spaced apart from one another to define the incubator path 58. The incubator also includes a floor 57 for supporting the bottom of the reaction vessels 52 and means for controlling temperature. The incubator is desirably maintained at a uniform, elevated temperature to ensure reproducibility of test results and to optimize reaction kinetics. Desirably, the temperature of the reaction mixtures in the reaction vessels is maintained at about 37° C.±1° C. In a preferred embodiment, the parallel walls 56 of the incubator are maintained at the desired temperature and heat the reaction vessels and their contents by convection. In order to assure uniformity of temperature along the length of these walls, they should be formed of a material which conducts heat rapidly, with aluminum being particularly preferred. Preheating sample liquid or reagents using the probe of the assay constituents delivery means before dispensing them into the reaction vessels will help to assure a uniform temperature is maintained within the reaction vessel.

The incubator belt shown as 54 in FIG. 2 comprises an elongate, endless tape 62 which extends along the entire length of the incubation path 58 at a position disposed generally above the floor 57 of the incubator. This tape should be flexible so that it may travel around the corners of the incubation path. The tape is adapted to carry a series of spaced-apart carriers 64 along its length. Each carrier includes a connector 66 for connecting the carrier to the tape 62. The carriers may be removably attached to the tape so that they can be easily replaced without having to replace the entire incubator belt 54.

The carrier 64 also includes a pair of spaced, parallel fingers 68 which depend downwardly from the connector 66. These fingers are spaced apart from one another a distance slightly greater than the width of a reaction vessel 52 so that a reaction vessel may pass between the fingers without undue resistance. The spacing between the fingers should not be too great, however, because the fingers are positioned to help support a reaction vessel in a generally vertical position, as shown. The parallel walls 56 of the incubator are desirably similarly spaced to provide additional support to the reaction vessels. Each reaction vessel 52 rests upon the floor 57 of the incubator, and the parallel fingers 68 of the incubator belt carrier and the parallel walls 56 support the vessel in a generally vertical position as it is moved along the incubation path.

The carriers 64 of the incubator belt are desirably spaced apart from one another along the length of the tape 62 to form a space 65 between adjacent fingers 68 of adjacent carriers 66. This space 65 should be sufficiently wide so that a reaction vessel may freely pass through without having its progress obstructed, but narrow enough so that the carrier fingers can support a reaction vessel in a generally vertical position. These spaces 65 will be referred to as "empty" positions and are desirably alternately positioned with respect to carrier positions along the entire length of the belt.

Figure 3:
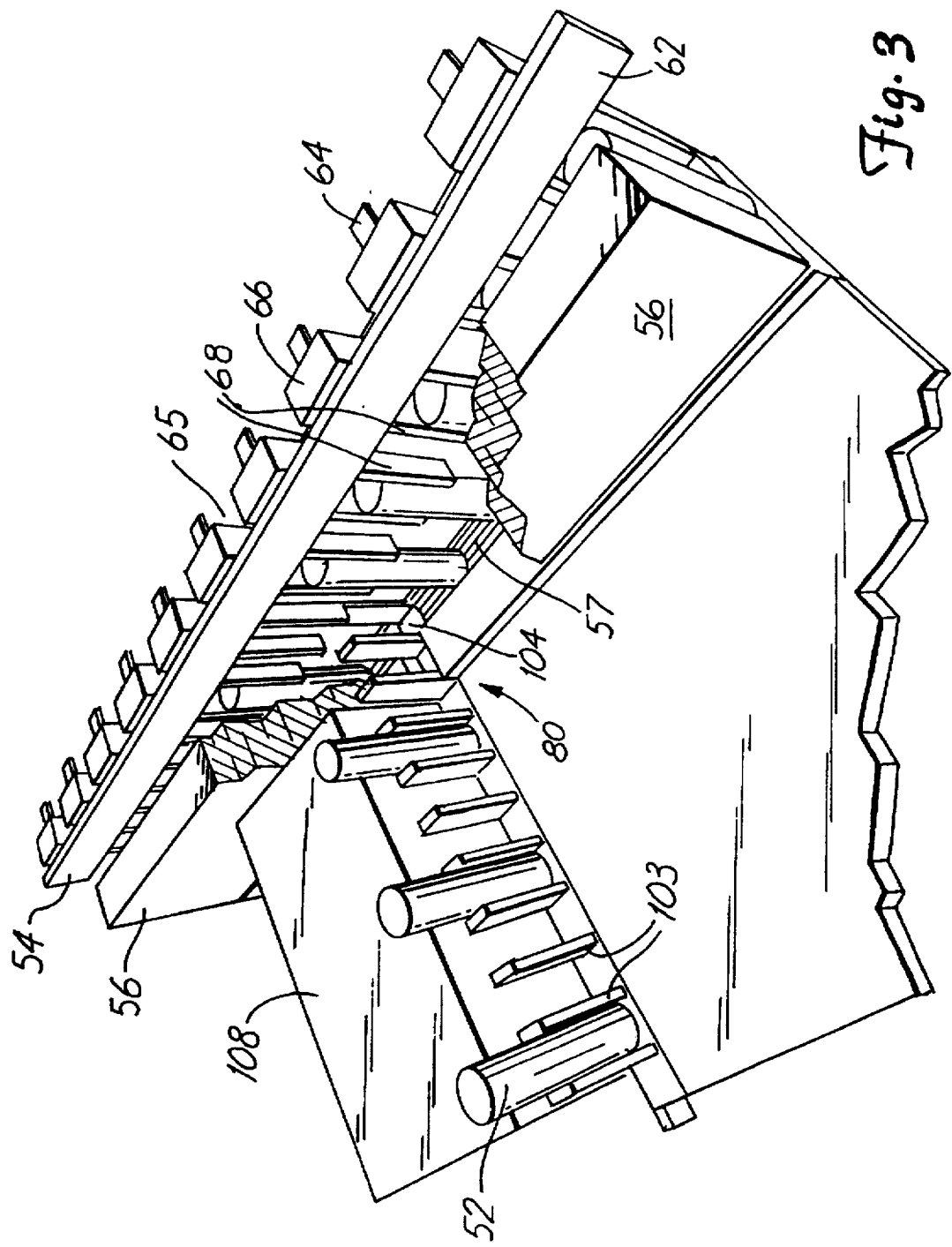
FIG. 3 is a perspective isolation view of a portion of the analyzer of FIG. 1 showing a portion of the incubator belt and the wash wheel and the interaction therebetween.
Figure 4:
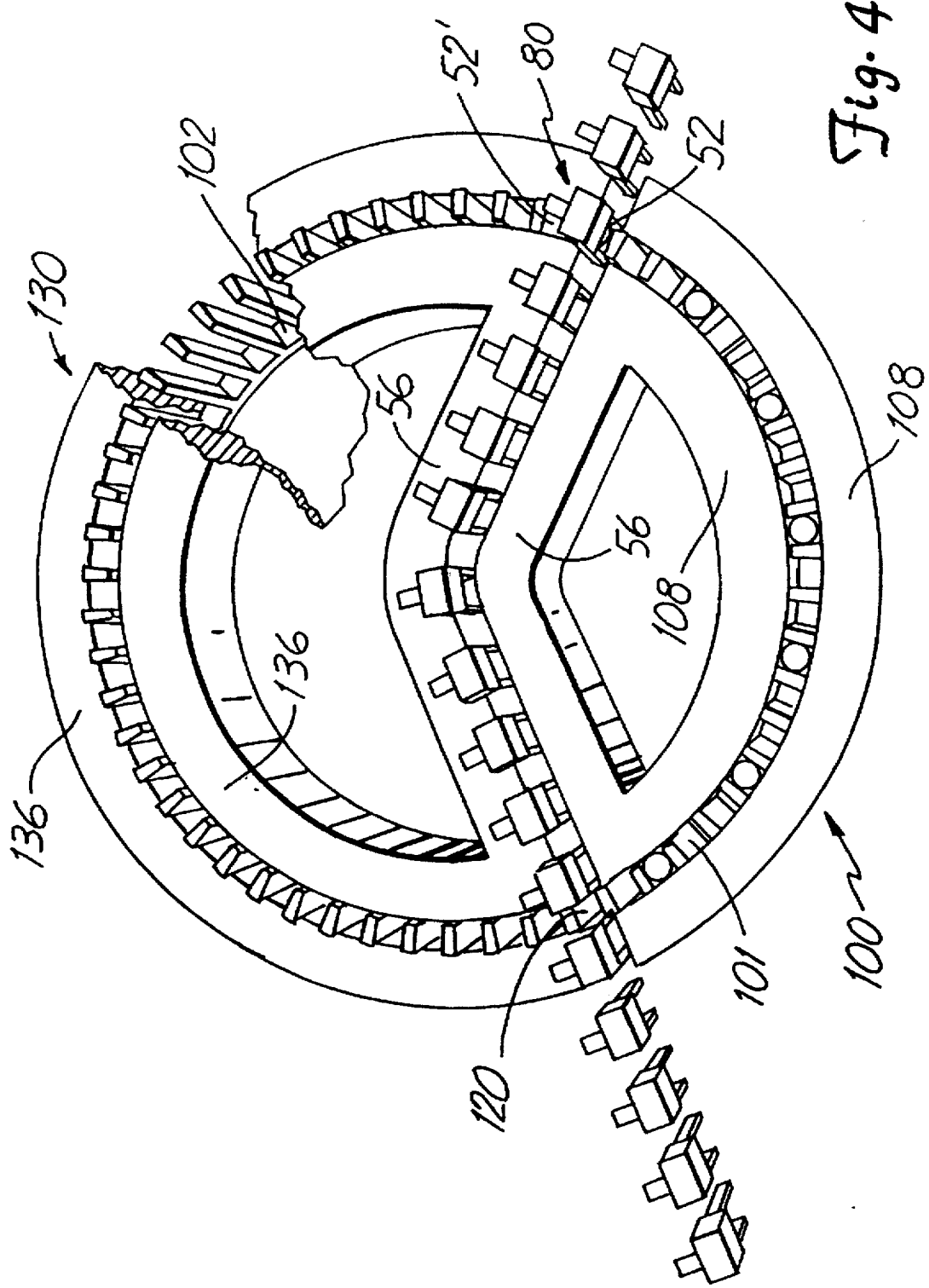
FIGS. 4-8 are schematic, perspective views of a portion of the analyzer of FIG. 1, showing transfer positions between the incubator belt, the wash wheel, and the read station.

Another assay resource of an analyzer of this invention is the wash station 100. As mentioned above, in a preferred embodiment, the wash station and the read station is each positioned in the analyzer in a manner such that reaction vessels will be transported along a predetermined path and at predetermined positions along that path the reaction vessels will be acted upon by the wash station and/or the read station. As shown in FIG. 4, the reaction vessels are transported along this predetermined path 101 by a rotating component 102, which will be referred to as the wash wheel. The wash wheel (FIG. 3) includes a floor 104 for supporting the bottom of a reaction vessel, a series of parallel, spaced-apart fingers 103 for supporting diametrically opposed sides of the vessel and parallel walls 108 for supporting the other opposing sides of the vessel. As in the incubator, the walls may be heated to maintain a substantially constant, elevated temperature if desired.

Unlike the incubator belt which is adapted to receive a vessel only at alternating positions along the belt, the wash wheel is desirably adapted to receive a vessel between each set of fingers along its path. This may be accomplished by providing equal spacing between the fingers 103 along the wash wheel path rather than using an uneven spacing format such as is used along the length of the incubator belt. Additionally, where the fingers 68 of the incubator belt depend downwardly, the fingers 103 of the wash wheel are attached to the floor 104 and extend generally vertically upwardly. The floor and the fingers are adapted to move together to move vessels along the wash wheel path. This may be accomplished by the floor being fixed in place on the wheel so that the fingers move as the wheel turns. Alternately, the floor may move independently of the wheel, the wheel desirably being fixed in place, and the fingers could be attached to the floor so that when it moves reaction vessels carried by the fingers will be transported along the path. Although the floor 104 may be flexible so that it may follow a complicated path, in a preferred embodiment the wash wheel is round and the floor is a rigid annular ring. If so desired, the upwardly extending fingers 103 may be integrally formed with the floor 104.

In a particularly preferred embodiment of the invention, the analyzer of the invention includes a novel method of moving reaction vessels between two transport mechanisms. In this embodiment the transport mechanisms are the transport means that are adapted to move reaction vessels along the wash wheel and incubation paths. Desirably the wash wheel path and the incubation path intersect at two transfer stations. FIG. 3 is a partially broken-away view of the first wash transfer station 80. At this transfer station, the incubator belt 54 and the wash wheel path 101 overlap permitting a vessel to be transferred from the incubator to the wash wheel. As shown in FIG. 3, when a vessel is ready to be transferred, the wash wheel will be positioned with respect to the incubator belt so that a pair of the wash wheel fingers 103 are disposed adjacent opposite sides of the floor 57 of the incubator and generally between two fingers 68 of the incubator.

It should be noted that the wall 56 of the incubator has been broken away in this view to show the overlap between the wash wheel path and the incubator path. In actuality, the gap in the wall 56 through which the wash wheel fingers pass is only slightly wider than the floor of the wash wheel. This permits opposing sides of a vessel on the incubator to be continuously supported as it moves along the incubation path onto the wash wheel floor, either by the walls 56 of the incubator or the fingers 103 of the wash wheel.

As mentioned above, although in the embodiment shown the read and wash stations are both positioned along the endless path of a wash wheel, the read and wash stations may each be positioned elsewhere in the apparatus. For example, the wash station may be positioned adjacent one wheel and the read station may be independently positioned adjacent a second wheel. Reaction vessels transported by the incubator belt 54 could be transferred to the wash and read stations on the separate wheels by any known means, such as a mechanical arm which will lift the vessel from one belt and place it on another belt.

In the preferred embodiment shown, both stations are positioned along one path and on one wheel, thus decreasing the number of transfers necessary during an assay.

Referring to FIGS. 3 and 4, when a reaction vessel 52 containing assay constituents on the incubator belt has completed its incubation, the vessel is positioned for transfer to the wash wheel. Moving the incubator belt 54 positions a carrier 64 carrying the vessel at the first wash transfer station 80. This disposes the vessel between two parallel fingers 103 of the wash wheel and onto the floor 104 of the wash wheel. The floor 104 of the wash wheel is desirably substantially aligned with the floor 57 of the incubator in order to permit the smooth passage of a vessel through the first wash transfer station.

Figure 5:
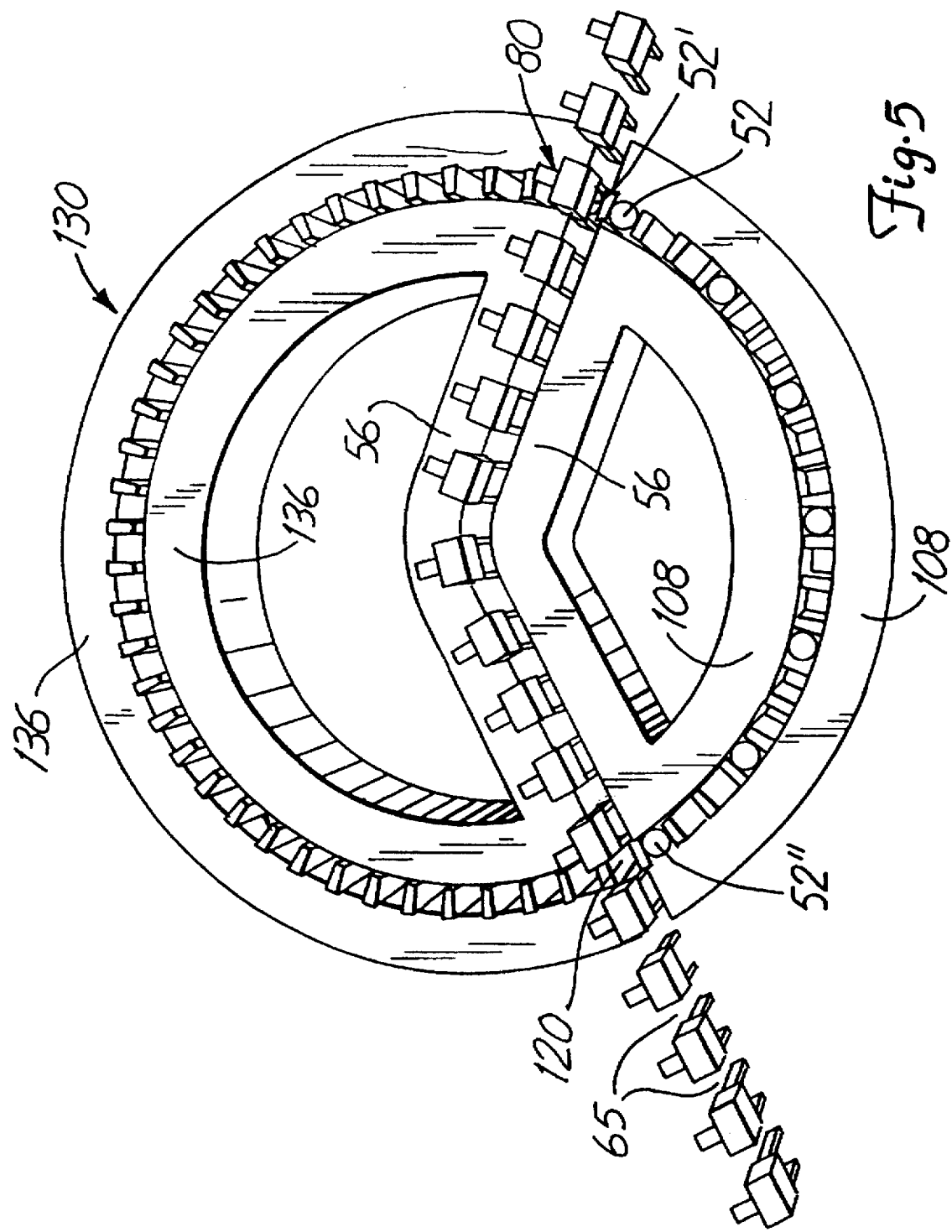

The wash wheel may then be indexed forward one position (i.e., moved clockwise as shown in FIGS. 4–8) to the position shown in FIG. 5. Since the fingers 103 of the wash wheel are oriented generally perpendicularly to the fingers 68 of the carrier at the first wash transfer station, the vessel will move with the wash wheel rather than remain in the carrier, therefore exiting the incubator and being transferred to the wash wheel. This leaves the carrier at the first wash transfer station empty.

A reaction vessel 52' containing a sample for which testing is completed and the detectable signal measured at the read station 130 is ready for removal from the analyzer. That vessel will be moved into the position on the wash wheel immediately preceding the first wash transfer station, as shown in FIG. 4. When the wash wheel indexes to move reaction vessel 52 from the incubator belt, the used reaction vessel 52' will move into the position previously occupied by the other reaction vessel 52 and into the empty carrier of the incubator belt.

Figure 6:
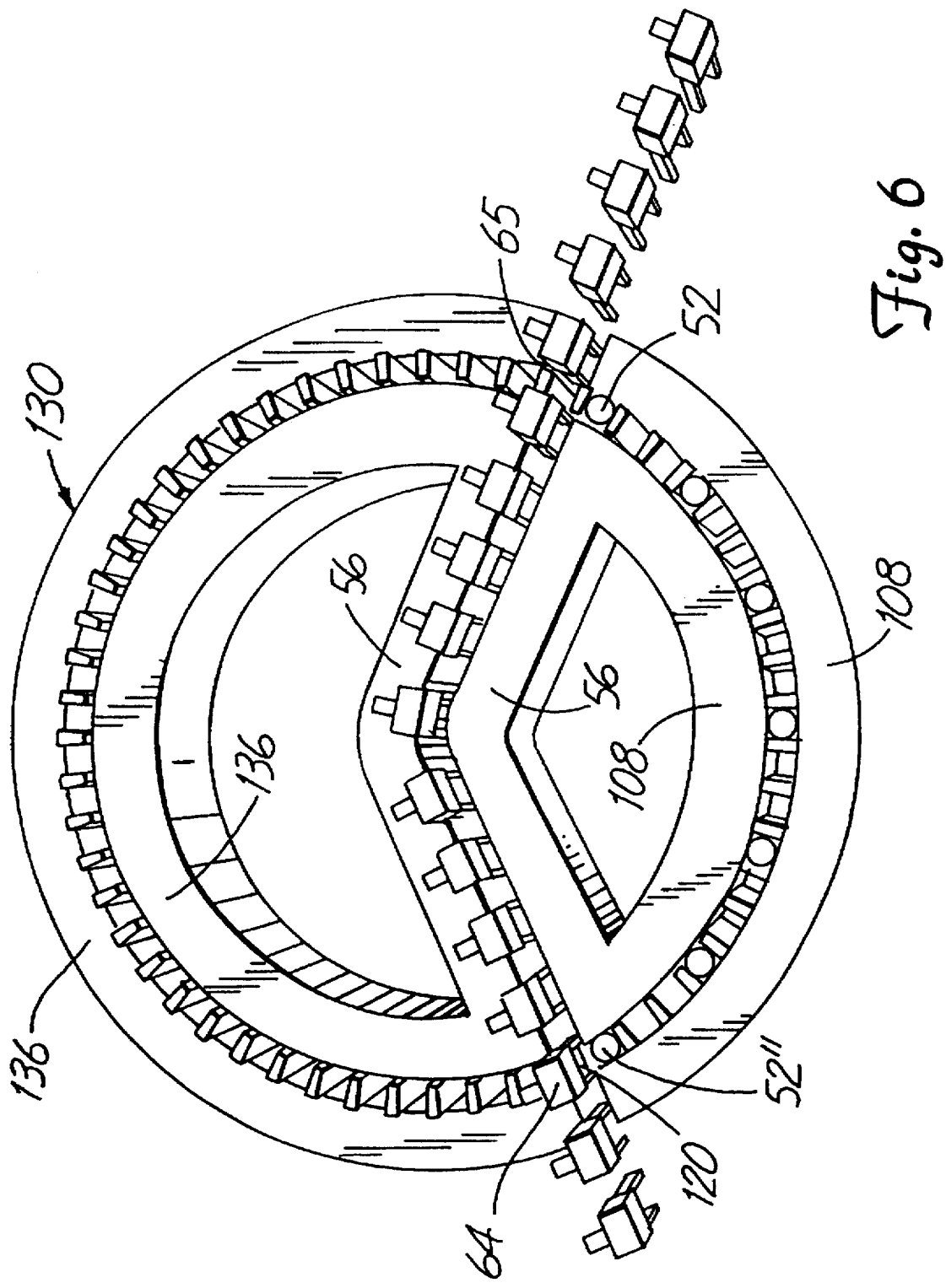

As shown in FIG. 6, the incubator belt is then indexed forward until an empty position 65 of the belt is positioned at the transfer station, and transferring the used reaction vessel 52' onto the incubator belt. After the used reaction vessel is transferred onto the incubator belt it is carried by the incubator belt to the incubation transfer station. When the vessel chain moves a vessel forward two positions, the used reaction vessel is transferred onto the vessel chain which becomes the vessel disposal chain. As the vessel chain is moved forward and back the used reaction vessel is transported to the waste chute 162. This waste chute leads to a waste collection container 164, where a number of used vessels may accumulate for later disposal. Although this waste collection container may take any desired form, it is preferred that it be of the type commonly used for medical waste. Preferably the container is provided with means for allowing a spent reaction vessel to enter the container while preventing the inadvertent withdrawal or removal of the vessel. The used vessel may be ejected from the vessel chain onto the chute 162 by a separate mechanism, such as the turnstile 166 shown in FIG. 1.

Referring again to FIGS. 4–8, the wash-cycle path 101 extends from the first wash transfer station 80 to a second wash transfer station 120. A wash station is desirably positioned adjacent the path 101. The wash station in this embodiment includes six locations where the reaction vessel may be acted upon. When a vessel is transferred onto the wash wheel at the first wash transfer station 80 it is indexed forward through the wash cycle which in this embodiment includes a plurality of positions where the vessel is acted upon. In a preferred embodiment, if a wash and separation step is required at all for a particular assay the following occurs as the reaction vessel is indexed ahead one position during every cycle of the wash wheel. At the first position following the first wash transfer station 80, liquid dispensing means (not shown) add a predetermined amount of wash solution to the reaction vessel and the contents of the vessel. The reaction vessel is then indexed forward to a position on the wash cycle having a pair of magnets (not shown) mounted on opposing walls of the wash-cycle path which cause the magnetic particles to be pulled from solution. Aspirating means (not shown) at this position along the wash-cycle path then withdraw the liquid from the reaction vessel. In the embodiment of the invention described here, the reaction vessel is indexed forward through a total of six positions, three positions where wash solution is added and mixing occurs alternating with three magnetic separation-aspiration positions.

Liquid dispensing means useful with this invention include any probe or pipetting means known in the art. In this embodiment, the liquid dispensing means includes three probes or tubular pieces, each probe being capable of moving downwardly into a reaction vessel so that a predetermined amount of liquid may be dispensed therein. The probes are attached to a source of wash solution and in a preferred embodiment the three probes are mounted on a carrier (not shown) that will move the probes downwardly simultaneously. Thus, in the preferred embodiment three reaction vessels may be washed simultaneously. The aspirating means of this embodiment is similarly constructed.

Desirably while at the position where wash solution is added to the vessel, the contents of the vessel are mixed. In the embodiment of the invention described here, mixing is accomplished as a spinning means (not shown) descends to the vessel and is releasably attached to the opening at the top of the vessel. The spinning means spin the vessel in one direction and then the other direction to suspend the particles in the wash solution. Other mixing means are well known in the art. For example, a mixer may be attached to the liquid dispensing means and rotated to mix the vessel contents, or the liquid dispensing means may be a ultrasonic probe such as that described above.

As shown in FIG. 6, when an empty position 65 is located at the first wash transfer station, a carrier 64 is located at the second wash transfer station 120. During the next cycle, the wash wheel is indexed forward (clockwise) one position, so that a washed reaction vessel 52" is positioned in an incubator belt carrier 64 at the second wash transfer station. The configuration of the second wash transfer station is essentially identical to that shown in FIG. 3 for the first wash transfer station. Accordingly, a vessel may be transferred from the wash wheel back onto the incubator at the second wash transfer station by indexing the incubator belt forward during the next cycle. The indexing of the wash wheel and incubator belt is controlled in accordance with a method of the invention which will be described in detail below.

Figure 8:
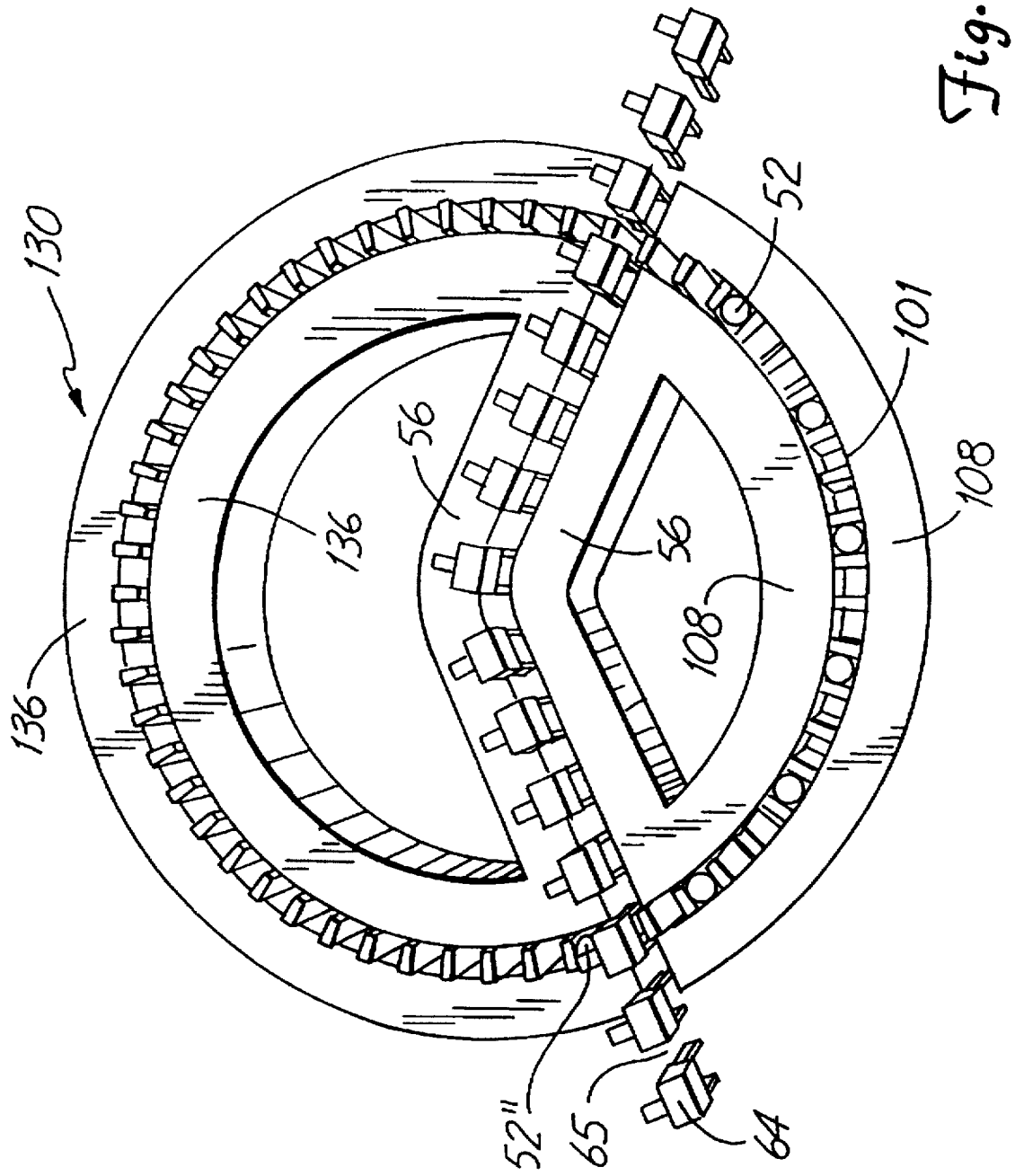

If the read station were physically separated from the wash station, the vessel would always be transferred either to the incubator belt from the second wash transfer station or directly to a belt or conveying device which would transport the reaction vessel to the read station. In the preferred embodiment of the invention, the read station is positioned along the wash wheel path and physically integrated with the wash wheel 102, as explained below. Accordingly, when a reaction vessel containing assay constituents has completed all of the necessary incubating and washing steps, it may remain on the wash wheel and proceed through the second transfer station to the read station, as shown in FIG. 8. This may be accomplished by keeping the incubator belt stationary until the wash wheel goes through another indexing cycle and advances one more position. The vessel will then simply pass through the stationary carrier at the transfer station without leaving the wash wheel. Even if the incubator belt must be moved between movements of the wash wheel, such as to carry out other operations, the same result can be achieved by repositioning the washed reaction vessel 52" back at the second wash transfer station before the wash wheel indexes again.

As previously noted, in some analyte tests, the protocol requires a wash step and then the addition of additional reagents or a dilution step before a second stage of processing. In such a case, the incubator belt 54 may be moved when the system is in the position shown in FIG. 7 to transfer the washed vessel 52" to the incubator belt. The incubator belt should be moved to position the vessel 52" at the incubator transfer station 160 so it can be transferred onto the vessel chain 70 for the addition of various reagents. An empty carrier 64 should then be positioned at the second wash transfer station before the wash wheel indexes forward to ensure that a vessel will not be prematurely transferred to the read station.

One other instance when it may be desirable to transfer a reaction vessel which has been washed back to the incubator at the second wash transfer station is when the sample needs a longer incubation period after the wash step than is permitted along the wash-cycle path 101. As explained before, the wash wheel moves in a lock-step fashion, preventing any significant variation in the time parameter of the washing or reading functions.

When a reaction vessel is carried through the second wash transfer station to the read station a substrate addition station may be positioned along the path so that substrate necessary to cause the assay constituents to yield a detectable signal may be added. Some forms of detectable signal do not require the addition of a substrate; the analyzer could, for example, be adapted to detect a fluorescent or radioactive label. In the preferred analyzer, the detectable signal is based upon chemiluminescence. Accordingly, substrate for the generation of a luminescent signal in an enzyme assay must be added. In the preferred analyzer shown in FIG. 1, substrate is added to the reaction vessel by means of a substrate pump (not shown). A suitable substrate is supplied to the pump and the pump may be adapted to dispense a predetermined volume of substrate into the reaction vessel.

Substrate reactions for producing a chemiluminescent signal generally require that the substrate and assay constituents be maintained at a relatively constant, elevated temperature. It is preferred, therefore, that the walls 136 of the portion of the wash wheel adjacent the read station be maintained at a constant, elevated temperature. The substrate addition station desirably includes a substrate dispensing means, such as a probe, that is heated so that the substrate added to the reaction vessel is heated to the appropriate temperature.

As shown in the figures, the read station 130 comprises a light-detecting means 140, e.g., a photomultiplier, positioned along the wash wheel path at a position adjacent the first wash transfer station 80.

The light detector may be a photomultiplier tube designed to detect a specific desired wavelength of light. When a vessel containing assay constituents is located on the wash wheel immediately adjacent the photomultiplier tube, the tube can monitor the luminescence of the assay constituents for a predetermined period of time to detect a specific wavelength of light being emitted. The signal detected by the photomultiplier tube is desirably conveyed to the controller 200 to be either printed out for the user or further processed by the controller. The controller desirably includes a series of analyte-specific calibration curves for correlating the measured luminescence of the assay constituents to the quantity of analyte originally in the patient sample. This signal may then be delivered to the operator as a final test result. If so desired, the controller may be programmed to reconduct the desired test on a particular sample by diluting the patient sample if the signal generated by the sample is too great to provide a reliable test result, such as when the detected signal is off the scale of the calibration curve.

Once the assay constituents of a reaction vessel have moved through the read station, the vessel is indexed forward to the first wash transfer station. As explained above, the vessel may then be transferred to the incubator belt and moved to the incubator transfer station where it is transferred to the vessel chain for disposal. When the wash wheel is indexed forward three times as shown in FIG. 8, a reaction vessel on the incubator belt that has completed its incubation may be positioned at the first wash transfer station, as shown in FIG. 4. This final movement of the incubator belt completes one full indexing cycle of the incubator. During this same period of time the wash wheel has indexed forward three times, i.e., completes three of its indexing cycles.

In the novel method of automatically analyzing samples of this invention, only one reaction vessel containing assay constituents may be transferred from the incubator to the wash wheel during an indexing cycle of the incubator. Accordingly, one reaction vessel is positioned in every third position of the wash wheel, with the intervening wash wheel positions desirably remaining empty. This, in turn, dictates certain geometrical spacing requirements of the analyzer.

The incubator should be configured such that the distance along the incubation path between the first and second wash transfer stations is equal to an odd number of positions along the incubator belt. Stated another way, if one pitch of the incubator belt is defined as the distance between one carrier and the next adjacent carrier, the distance between the first and second transfer stations should be m+½ pitches, wherein m is an integer. This ensures that whenever an empty position 65 is at the first wash transfer station, a carrier will be positioned at the second wash transfer station, and vice versa. This permits the wash wheel to move as described above without prematurely transferring a vessel from the incubator to the wash wheel path or inadvertently transferring a vessel from the incubator to the wash wheel path leading to the read station. If the spacing differs, either the wash wheel or the incubator belt could fail to align properly at the wash transfer stations at the proper time, preventing one or the other from moving. Alternatively, the apparatus could position a carrier 64 at both of the transfer stations at the same time mechanically, but that would prevent the maximization of resource utilization obtained when all of the carriers carry a vessel for incubation.

The number of positions on the wash wheel and the number of those positions that lie along the portion of the wash wheel path that passes through the wash station can vary quite widely. The number of positions will depend upon the number of functions that are to be performed on reaction vessels along that portion of the path as well as the dwell time necessary for vessels moving along the portion of the path that passes through the read station. The relative proportions of the wash portion of the path and the read portion of the path need not be those shown in FIGS. 4–8.

Regardless of the overall number of positions on the wash wheel and the number of those positions that are on the wash portion of the path or the read portion, the total number of positions on the wash wheel and along the wash portion of the path must be a multiple of three plus one additional position (3n+1), if, as here, the incubator belt's indexing time is 3 times as long as the wash wheel indexing time. It should be understood though that if the indexing time of the incubator belt is increased such as to 4, 5 or more that the multiple used to determine the number of positions on the wash wheel must be similarly changed. For instance, if the indexing time of the incubator belt is 4 times the wash wheel indexing time, the formula for determining the number of positions should be (4n+1). In the analyzer shown in FIGS. 4–8, there are 55 [(18×3)+1] positions along the length of the wash wheel, with 19 [(6×3)+1] positions being disposed between the first and second wash transfer stations. Although the embodiment of the invention described herein shows the relationship between the wash wheel transport means and the incubator belt transport means, this method of transferring vessels between two transport mechanisms can be used in other embodiments where materials must be transferred between two such mechanisms.

Figure 7:
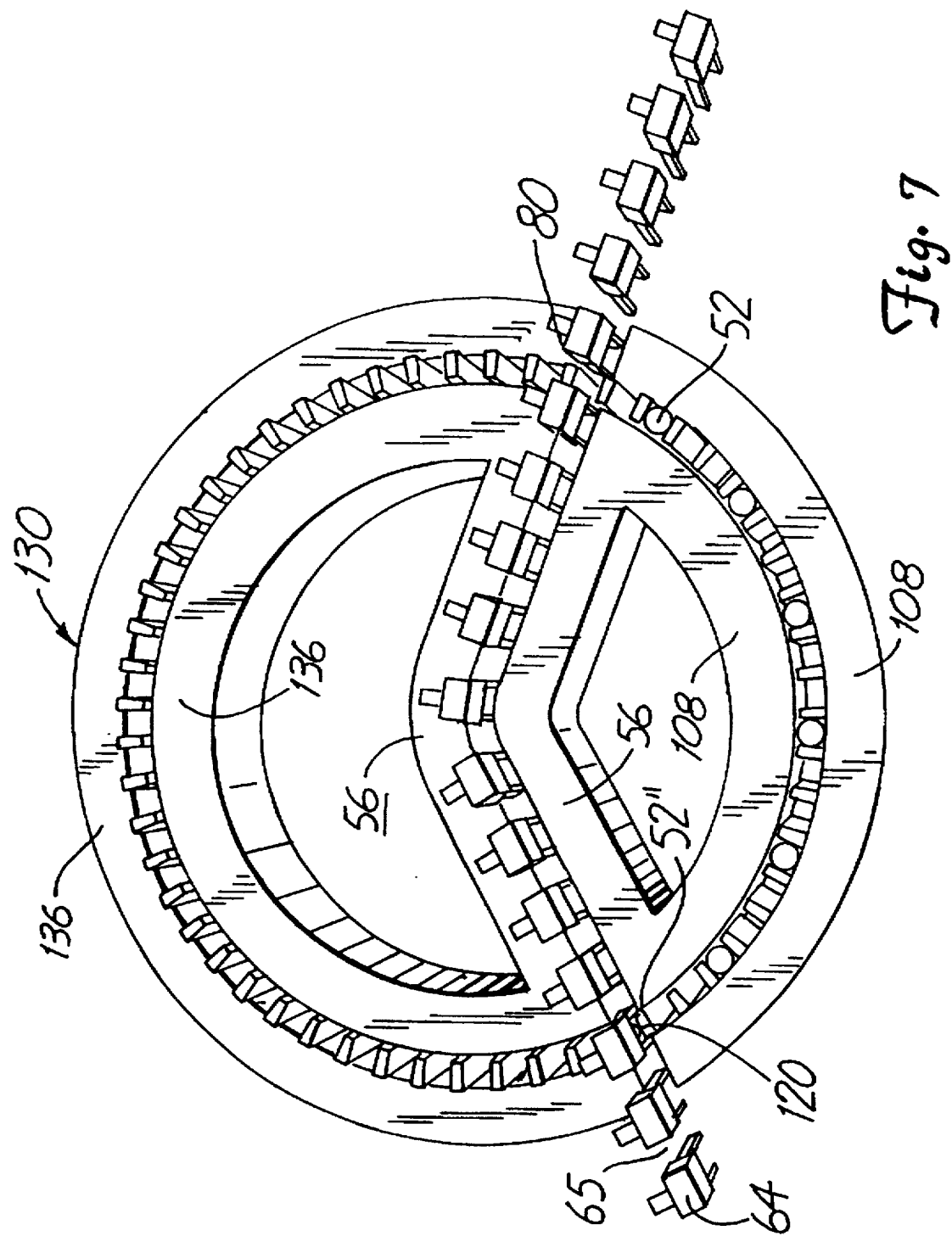

In order for the desired interaction of the incubator belt and the wash wheel at the first and second wash transfer stations to occur, the number of positions on the wash wheel must be one position greater than a multiple of three positions. Referring to FIG. 5, a used reaction vessel 52' is positioned for transfer back to the incubator belt. In order for this transfer to take place, the incubator belt must be free to move. If the number of locations were an integral multiple of three, the washed reaction vessel 52" would be at the second wash transfer location and disposed at an empty position 65 on the incubator belt. When the incubator belt moved to remove the used reaction vessel 52', the washed reaction vessel 52" would be transferred to the incubator path at that empty position 65. By adding one additional position to the wash wheel, the incubator is free to move into the position shown in FIG. 6 and the wash wheel may then be indexed to transfer the washed reaction vessel 52" to the incubator belt, as shown in FIG. 7.

As mentioned above, the analyzer and method of the invention are based upon a unique scheduling and timing method implemented by analyzer control means. In use, once a reaction vessel is filled with assay constituents, the reaction vessel will transfer onto the incubator where it will remain for a predetermined number of indexing cycles. The number of cycles will be analyte test-specific and readily varied from one test protocol to another. In the preferred embodiment, each indexing cycle lasts for the indexing time and the desired incubation time of the test protocol can be expressed as a multiple of that time. Once the reaction vessel containing assay constituents has been incubated for the specified time, the analyzer control means causes it to move to the first wash transfer station 80 for transfer to the wash wheel 100. The analyzer control means then cause the wash station to act on the reaction vessel as it is moved along the wash-cycle path, where the functions are timed on a cycle-by-cycle basis.

The analyzer control means comprises transfer control means, and scheduling means each of which comprises a computer program or a subroutine of a computer program, associated electronics and means of connecting the operative elements of the analyzer to the control means. The computer programs and the associated computer functions are included in the electronics of the analyzer and generally include a microprocessor, a hard disk and a floppy disk drive. The analyzer control means provides an interface into the apparatus through which it is possible to define the operations required to process a sample of any particular chemistry type and in any chronology. Assay data may be stored in data files of the computer program on the hard disk and may be subsequently retrieved for performing the desired assay. The stored data, includes the mechanical assay requirements such as the control of electro-mechanical devices, the timing requirements of those devices, reagent package location and other such requirements. In addition to stored data, other data (calibration values, standard values, default control, etc.) may be entered via the keyboard associated with the analyzer for interface with the computer program. The floppy disk drive is used to add new information to the hard disk. The electronics of the analyzer control means typically include printed circuit boards that control such elements as the motor drivers, ultrasonic transducer, heaters, temperature sensors, and luminometer.

The analyzer of the invention desirably includes a computer monitor having a display screen on which the computer program displays information to the operator and information guiding an operator in inputting sample identification information. In addition to providing sample identification information and analyte test requests into the computer, the operator can instruct the computer give the processing of a particular sample high priority.

When a tray of reagent packages or sample cups is placed in the analyzer, the bar code label information may be read and fed to the electronics for processing by the computer program. In the analyzer shown in FIG. 1, 6 sample trays, each containing 10 samples, can be processed at one time. Each sample will be assigned a tray position as it is placed in the analyzer and the information identifying the sample and the tests to be performed on the sample enter by the operator. Each newly entered test request is stored in a computer file referred to herein as a worklist, with all the other test requests in progress or pending. The tests requests are processed by the analyzer control means as described below.

Figure 9:
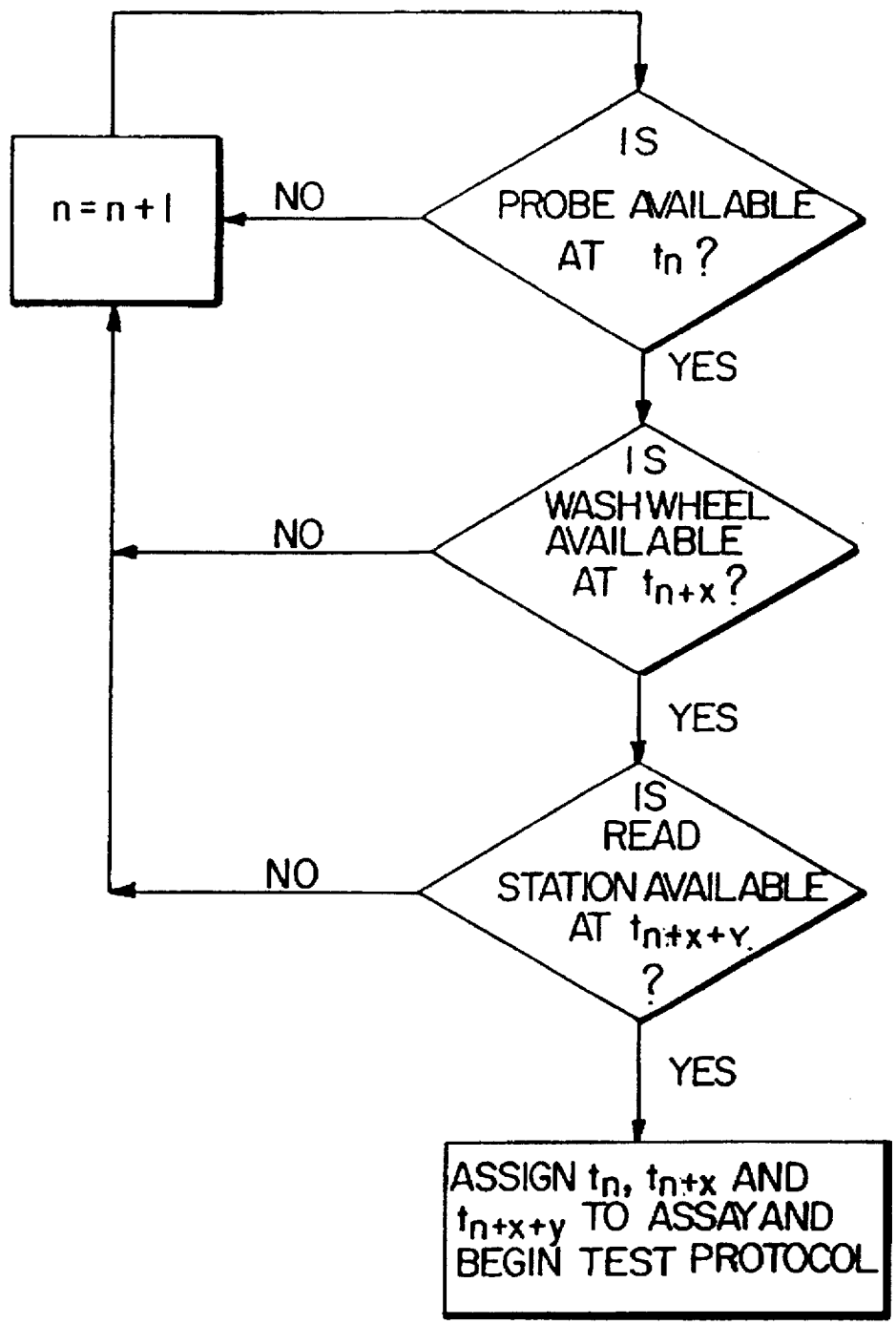
FIGS. 9 and 10 are flowcharts depicting the scheduling logic of an embodiment of the invention for one-stage and two stage assays, respectively.
Figure 10:
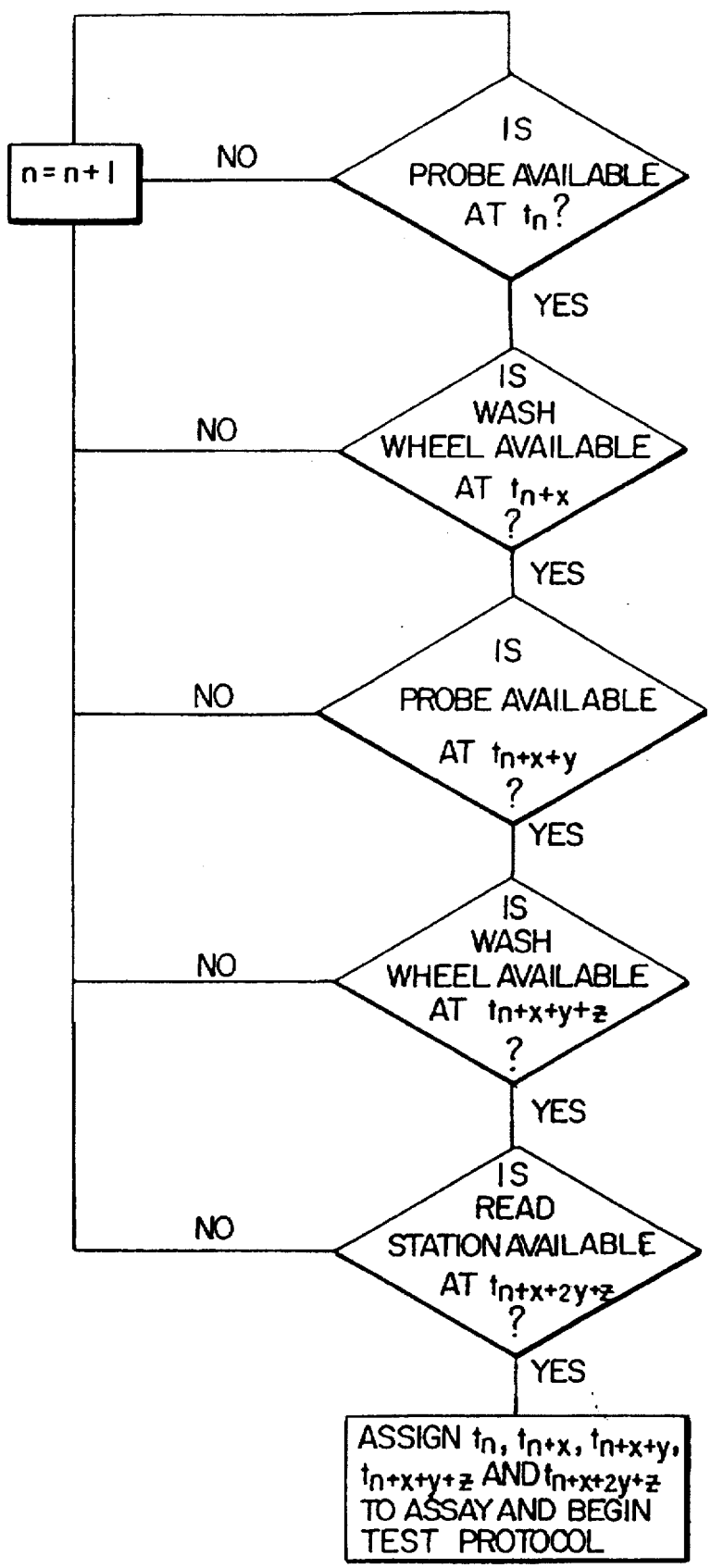

FIGS. 9 and 10 show flow charts of the scheduling logic of an analyzer control means 200 of the preferred analyzer and FIG. 11 depicts an actual scheduling sequence for six samples. Referring first to FIG. 9, this flow chart depicts the scheduling logic for a test having a one-stage assay protocol, i.e., a protocol where the assay constituents in a reaction vessel are incubated, washed and read sequentially. First, the control means determines whether the assay resource or resources necessary to begin a desired test is available at the start of the next cycle of the analyzer, which in this embodiment is the start of the next incubator cycle in the preferred analyzer described herein, the first assay resource that must be available is the assay constituents delivery means. If the delivery means is scheduled to be performing another function at that time, such as delivering reagents to a reaction vessel containing assay constituents of a two-stage protocol test, the control means will check successive cycles to determine the first available cycle when the assay constituents delivery means is available.

When an available cycle for the delivery means to operate has been identified, the controller determines whether transfer to the wash wheel and the wash station operations will be available at the appropriate time to act on the reaction vessel if the delivery means began its operation during that first available cycle. As described above, in this embodiment the dwell time of a vessel in the incubator can be expressed as a multiple of the indexing time of the incubator, i.e., an integral number of indexing cycles of the system. In FIG. 9, this number is denoted as "x" and the control means determines whether a position is available on the wash wheel that will take a reaction vessel through the wash station at "n+x" indexing cycles, or x indexing cycles after the assay constituents were added to the vessel. If a reaction vessel is already scheduled to enter the wash wheel at the "n+x" time slot, the control means determines the next available cycle for the delivery means, indexing "n" each time, until it determines that an "n+x" time slot will be available on the wash wheel if the assay constituents are added to a reaction vessel during the cycle when the delivery means is available.

Before processing of the test begins, the control means must also determine on a cycle-by-cycle basis when the reaction vessel can be transported to the read station. In this embodiment, a vessel will reach the read station an integral number "y" indexing cycles of the incubator after the vessel has been transferred onto the wash wheel at the first wash transfer station. Although "x" may vary between test protocols, "y" will be constant for all protocols because the wash wheel moves in a fixed cycle. If the read station is not available at the time slot "n+x+y", the control means will check the availability of all the assay resources on a cycle-by-cycle basis until a time when at initiation of processing at a time slot "n" all the necessary assay resources will be available at the appropriate time.

Once the control means determines a suitable initiation time slot "n" for a test, it will schedule the test to begin processing at time "n" and it will allocate the assay resources to that test according to the time-based requirements of each of the necessary assay resources. Thus, it will schedule the reaction vessel designated for that test to enter the wash wheel at time slot "n+x" and move to the read station at time slot "n+x+y". When the control means determines a suitable initiation time slot "n" for a second test, it must check the availability of the time-based assay resources requirements of that second test against the allocation of assay resources for any previous test.

FIG. 10 shows a similar flow chart depicting the scheduling logic of the control means for a test having a two-stage protocol. Comparing FIGS. 9 and 10, the first two scheduling steps are the same for a one-stage test protocol and a two-stage test protocol. After a reaction vessel has been acted upon by the wash station, it must be transferred back to the incubator belt where additional reagents may be added. Accordingly, as the next step in the scheduling logic, the control means must determine if the assay constituents delivery means, rather than the read station, is available at time "n+x+y." If the assay delivery means is available, the control means must check to see whether a position on the wash wheel will be available after a second incubation time "z". Finally, if a position on the wash wheel is available, the control means must determine if the read station will be able to act on the reaction vessel when it reaches that station. As discussed above, if a position on the wash wheel is available, generally, the read station will be available. When a suitable initiation time slot has been determined by the control means, it will allocate the necessary resources to that test, preventing scheduling of subsequent tests for the assay resources at those time slots.

FIG. 11 shows an exemplary schedule for a series of six patient tests. Tests 1, 2 and 6 are each two-stage assays having first and second incubation times of five indexing cycles. In the preferred embodiment, the indexing time of the incubator is 36 seconds, resulting in incubation times of approximately three minutes. Tests 3, 4, and 5 are all one-stage assays having incubation times of eight indexing cycles, or in the preferred embodiment, incubation times of about 4 minutes and 48 seconds.

In this hypothetical schedule, the tests are conducted in order of their sample numbers. Since no other tests have been previously scheduled, test one of sample one is immediately initiated and the time-based assay resources necessary for its processing are allocated to it on a cycle-by-cycle basis, with its processing beginning at indexing cycle "0". The test protocol requires a five indexing cycle incubation, so x equals 5. The reaction vessel containing the assay constituents is scheduled therefore to be transferred from the incubator belt at the first wash transfer station and enter the wash wheel at the fifth indexing cycle. In this embodiment, the reaction vessel will be transported through the wash station from the first wash transfer station to the second wash transfer station in approximately 3 minutes. In the preferred embodiment, the incubator indexing cycle is three times the wash wheel indexing cycle. Therefore, in 15 wash wheel cycles or 5 indexing cycles, the reaction vessel will be positioned adjacent the second wash transfer station with a 36-second indexing cycle, this yield a time of about three minutes during which the vessel is moved along the wash-cycle path. The control means has scheduled the assay constituents delivery means at time slot 10 to dispense additional reagents into the reaction vessel, denoted in FIG. 11 as 1.2 and positioned on the vessel chain and transfer the vessel back to a position on the incubator belt. The reaction vessel is then transferred back onto the wash wheel at indexing cycle number 15. The reaction vessel will move through the wash station and then to the read station "y" indexing cycles later, or at indexing cycle number 20.

Since the second test has the same assay protocol as the first test, the control means will transport the vessel through the analyzer, allocating each of the necessary assay resources to it one indexing cycle after the indexing cycle allocated for the first test. Thus, the assay constituents for the second test will be delivered to a reaction vessel by the assay constituents delivery means at indexing cycle 1; the reaction vessel will be positioned to transfer to the wash wheel at indexing cycle 6; and the vessel will be transferred to the incubation transfer station and onto the vessel chain for addition of assay constituents at indexing cycle 11; the reaction vessel will be transferred to the wash wheel a second time at indexing cycle 16; and it will be transferred to the read station at indexing cycle 21.

Test three has a one-stage assay protocol. In this example, the incubation time for this test is 8 indexing cycles. Accordingly, the control means will first determine which time-based assay resources are required to process the test and it will then check the availability of those assay resources on a cycle-by-cycle basis against the allocation of the resources to the processing of tests one and two. Since the incubation time is eight indexing cycles the reaction vessel will be ready to transfer to the wash well at indexing cycle 10, eight indexing cycles after the test is initiated if it is initiated at indexing cycle 2. Neither of the reaction vessels of test one or test two is scheduled to be transferred to the wash wheel at indexing cycle 10 so processing of test 3 can be initiated at indexing cycle 2 if the read station will be available at indexing cycle 15; in the preferred embodiment this will always be the case. Test 4 and 5 in this example have one-stage protocols as did test 3. Hence, absent any conflicts in the allocation of assay resources, processing of the reaction vessels of tests 4 and 5 will sequentially follow the reaction vessel of test 3, by one or two indexing cycles respectively. As can be seen from FIG. 11, no scheduling conflicts exist for either test 4 or test 5 in this example.

In this example, test 6 has a two-stage assay protocol. The control means will first determine the time-based assay resources necessary for this test on a cycle-by-cycle basis. The control means will then check the allocation of assay resources to the tests in process to determine the availability of each of the necessary resources for test 6. In this example, the control means would identify a conflict if test 6 is initiated at indexing cycle 5. As shown in FIG. 11, the reaction vessel of test 3 is scheduled to be transferred to the wash wheel at indexing cycle 10, which is the same cycle the reaction vessel for test 6 would be scheduled for transfer to the wash wheel if initiated at indexing cycle 5. Since the control means has already allocated the wash station resource to test 3 at that time slot, the control means will begin checking for the availability of resources for test 6 if processing is initiated at indexing cycle 6. In this example, initiation of the processing of test 6 will be delayed until indexing cycle 8, when all the necessary assay resources will be available for processing test 6 at the appropriate time.

In the example shown in FIG. 11 the tests were processed in order of placement on the analyzer by the operator. In use, the control means of the analyzer advantageously optimize the scheduling of a plurality of analyte tests for patient samples for which the necessary identifying information has been provided. In the above example, the scheduling of the tests could be rearranged so that test 6 would be initiated immediately after test 2, and then tests 3, 4, and 5 would be initiated in each successive indexing cycle. Such scheduling by the control means reduces the overall number of indexing cycles necessary to complete the processing of all the tests thus decreasing total processing time and increasing throughput. The control means schedules tests to maximize throughput using an optimization routine.

Figure 12A:
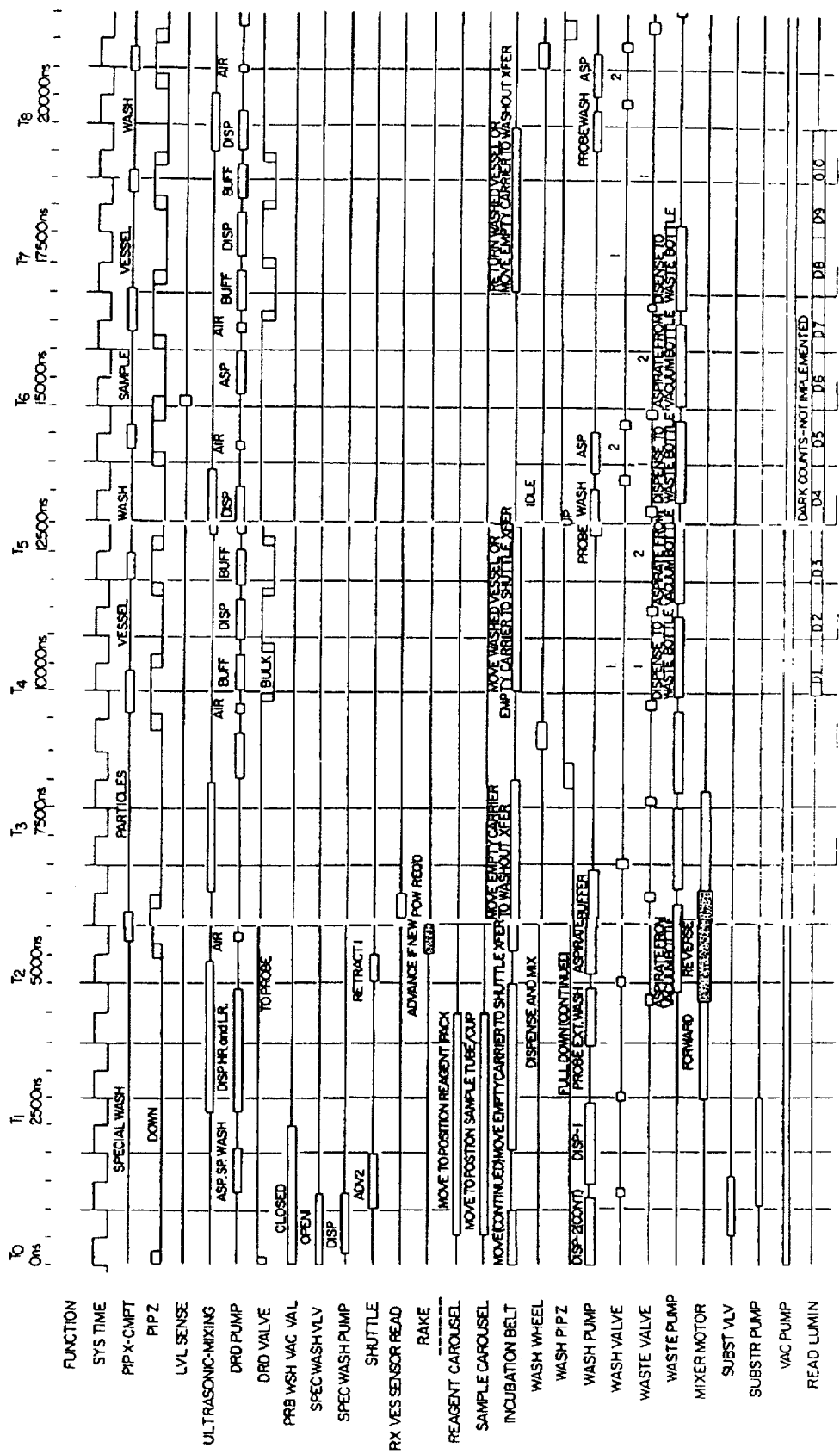
FIGS. 12A and 12B are portions of a timing diagram of operations occurring on the analyzer of FIG. 1.
Figure 12B:
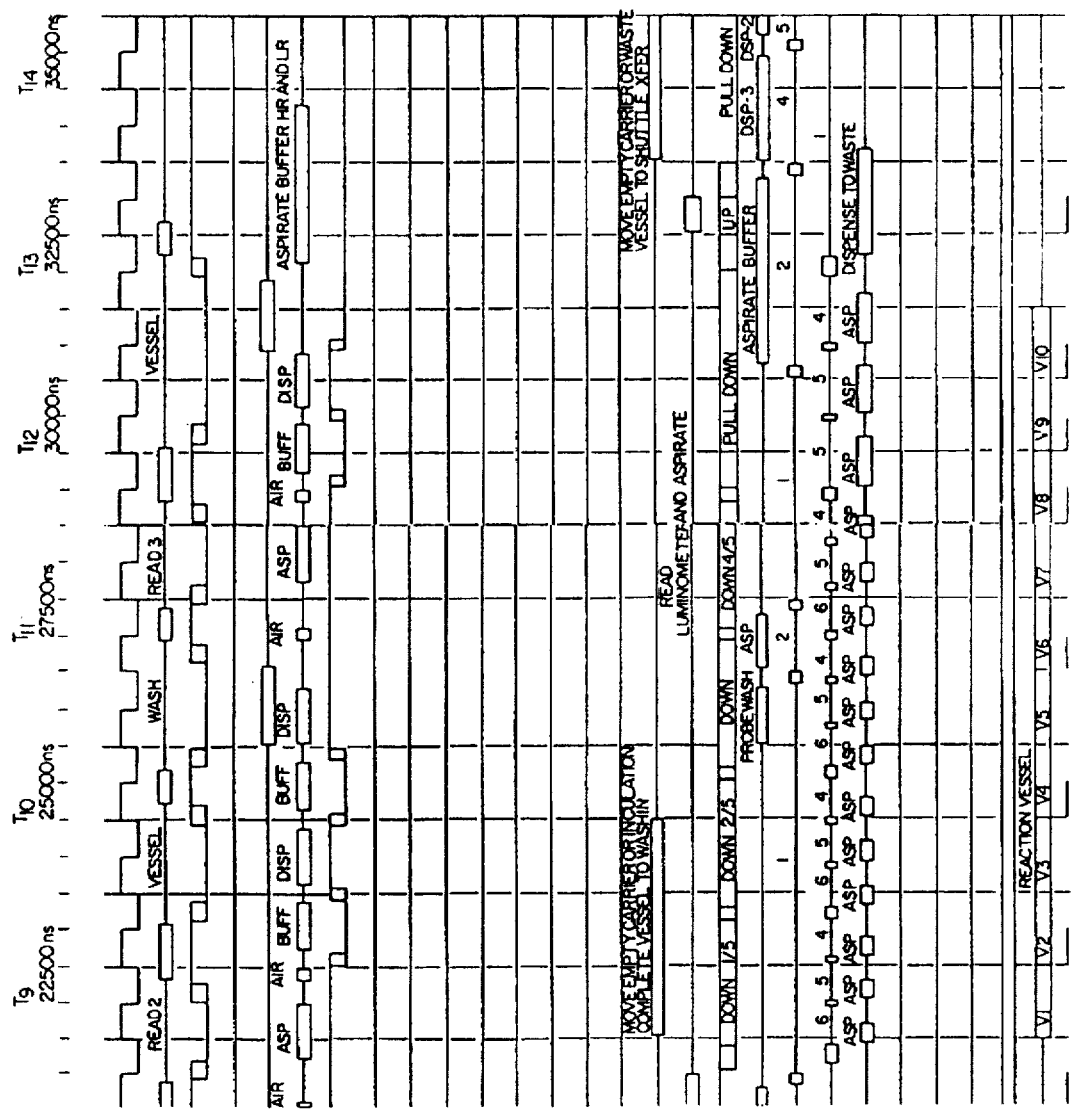

The method of the invention will be further described with reference to the timing diagrams of FIGS. 12A and 12B. As shown, a time line extends to the right of each analyzer element, with a broad band on the time line indicating a period of time during which the element operates and the narrower horizontal line indication when the element remains idle. The open boxes along some of the time lines (e.g., the "RAKE") represent time slots when the element may operate if necessary, but will not necessarily do so. One cycle of the analyzer is shown on 12A and 12B from $T_0$ to $T_0$. The fixed cycle may be of any length, although in this embodiment, one time division equals about 2500 ns.

As described above, a predetermined amount of sample and predetermined amounts of reagents must be transferred to a reaction vessel to initiate the processing of an assay. In a preferred embodiment, these assay constituents are transferred to the reaction vessel by the assay constituent delivery means, the means including a pipetting probe 42. The lateral and vertical movement of this probe are represented by the time lines in FIGS. 12A and 12B labelled PIP X-CMPT and PIP Z, respectively. The probe 42 is normally in its lowered position where it may be positioned within a well of a reagent pack, reaction vessel, sample cup or the like. As shown the probe is raised to its higher position as it is moved laterally so the probe will not strike the walls of a reagent pack or a reaction vessel.

Once the operator has entered information identifying a sample and the test to be performed on the sample, the analyzer control means will position the inner and outer carousels 22, 30 of the assay constituents supply wheel (designated as "reagent carousel" and "sample carousel", respectively) are move to position the desired reagent pack and sample cup for access by the probe. Starting at about $T_6$ the probe begins aspirating and dispensing volumes of sample and the necessary reagents to the reaction vessel. After each sample or reagent is dispensed into the reaction vessel, the probe is lifted up, moved laterally to the probe washing station 44, and lowered into that station. A cleaning solution, represented as buffer on FIG. 12, is dispensed through the probe into the drain cup.

Certain analyte tests are particularly sensitive to cross-contamination. For these tests, a special, more through washing procedure may be initiated before a second sample is transferred to the reaction vessel. This special wash is shown on FIG. 12 by the operation of the special wash pump (SPEC WASH PUMP) and corresponding special wash valve (SPEC WASH VLV). After the special wash, the pipetting probe is raised and moved to a reagent well where in this embodiment magnetic particles are stored. The reagent well could contain any reagent.

As described above, the probe may be ultrasonically activated to mix fluids, to level sense and to aid in cleansing of the probe. These operations are reflected in the time lines labeled "LVL SENSE" and "ULTRASONIC-MIXING". As shown in FIG. 12, the pipetting probe tip is ultrasonically activated at the end of each wash to aid in cleansing and drying of the probe. The probe is also activated when it is inserted in the reagent well containing the magnetic particles prior to aspiration of the particles.

The "PRB WASH VAC VAL" refers to probe wash vacuum valve that refers to the operation of a valve that turns on and off the vacuum associated with the probe washing station 44 in the embodiment described above.

The time lines labeled "DRD PUMP" and "DRD VALVE" represent the times in the operation of the analyzer when a pump such as the dual resolution pump used herein operates the aspiration and dispensing operations of the pipetting probe.

The "SHUTTLE" time line shows when the vessel chain 70 is operated to position a reaction vessel into position so that the assay constituent delivering means can dispense the assay constituents. As explained previously, a reaction vessel receiving assay constituents is desirably positioned on the vessel chain rather than on the incubator belt 54 to that the incubator belt may be moved during the pipetting operations of the probe. The vessel chain is retracted one position at about $T_2$ to properly position a new vessel for delivery. The probe will transfer sample and all the reagents required for the chosen analyte test to the reaction vessel during one cycle of the analyzer. The assay constituent containing vessel will then be prepared to be transferred to the incubator belt during the next cycle.

In order to transfer the reaction vessel to the incubator belt, the chain is advance two positions ("ADV2") and the incubator belt is indexed forward one position to permit transfer of the vessel to the belt. This movement of the incubator belt is shown along the time line labeled "INCUBATION BELT" between about $T_1$ and about $T_2$. "SHUTTLE XFER" refers to the incubation transfer station. As described above, if a washed vessel is moved from the wash wheel to the incubator belt at the "WASHOUT XFER" (second wash transfer station) and to the shuttle xfer as the shuttle (vessel chain) advances two positions the washed vessel will be positioned for disposal into the waste bag.

The "RAKE" time line refers to the movement of the plurality of fingers in the new vessel loader 72. A new row of vessels will be advanced only when necessary.

An important feature of a method of the invention can be seen by comparing the time lines and movements of the incubator belt and wash wheel. The wash wheel is advanced a fixed distance within each of its fixed-duration time cycles. As shown on the wash wheel time line, in a preferred embodiment the advancement occurs three times during each fixed cycle of the analyzer, in this embodiment one indexing cycle of the incubator belt. The wash wheel in the embodiment shown is advanced every five time divisions in FIG. 12, with a first advancement occurring at about $T_{3,4}$, the second movement at about $T_{8,4}$, and a third movement taking place at about $T_{13,4}$. It should be noted that in the embodiment shown, one analyzer cycle equals about 15 time divisions ($T_0$–$T_0$), the time between the third index of the wash wheel and its next indexing at $T_{3,4}$ of the next cycle, about five time divisions.

Comparing the incubator belt and wash wheel time lines shows that the two assay resources are never scheduled to move at the same time. When the wash wheel is moved the incubator belt remains stationary. The same is true of the vessel chain ("shuttle" in FIG. 12) and the incubator belt—they are never scheduled to move at the same time. At other times during the fixed cycle of the analyzer the incubator is free to move. This permits any desired vessel to move along the incubation path carried by the incubator belt to a desired transfer location without interfering with the operation of any other assay resource.

Six time lines shown in FIG. 12 reflect the timing of the operation of components associated with the wash cycle. The vertical movement of the pipette associated with dispensing wash solution and the operation of the associated pump and valve are depicted in the time lines labeled "WASH PIP Z", "WASH PUMP", AND "WASH VALVE", respectively. Similarly, the time lines labeled "WASTE PUMP" AND "WASTE VALVE", respectively are both associated with the aspiration of fluid. The time line labeled "MIXER MOTOR" indicates the operation of the mixing means described above in the description of a preferred embodiment. When mixing means of the type described herein is used, the motor causes the rotating means that removably attaches to the top of reaction vessel to rotate first in a forward, clockwise direction, and then to a counter-clockwise rotation, and then once again in a clockwise rotation.

The time lines of a substrate valve and substrate pump, ("SUBST VLV" and "SUBSTR PUMP") elements of the substrate delivery means are shown in FIG. 12.

The "VAC PUMP" time line depicts the continuous operation of a vacuum pump that supplies vacuum to those components of the analyzer requiring vacuum. The operation of the vacuum with respect to those components is controlled by the opening and closing of the respective valves.

The operation of the signal detecting means is indicated in FIG. 12 along the time line labeled "READ LUMIN". The luminometer is activated during the second indexing cycle of the wash wheel, when no reaction vessel is positioned adjacent the luminometer and a series of baseline measurements ("dark counts") are made. (As explained in detail the wash station and read stations of a preferred embodiment of the analyzer, are physically integrated on the wash wheel). The wash wheel then indexes forward placing a sample-containing reaction vessel adjacent the luminometer. The luminometer then takes a series of readings, measuring the signal generated. The amount of signal generated can be correlated with the amount of analyte present in the sample and a final test result obtained.

While a preferred embodiment of the present invention has been described, it should be understood that various changes, adaptations and modifications may be made therein without departing from the spirit of the invention and the scope of the appended claims.

What is claimed is:

1. An automated chemical analyzer for automatically analyzing a plurality of samples for at least two different analytes comprising:
   a) a plurality of assay resource stations each including an assay resource capable of performing a predetermined operation upon a sample-containing reaction vessel within a first indexing time, the first indexing time defining a time cycle of fixed duration, wherein a first of said assay resource stations is an incubation station comprising an elongated, movable transport means adapted to carry a plurality of reaction vessels along an incubation path, a second of said assay resource stations is a wash station including a movable transport means adapted to receive and carry a plurality of reaction vessels along a wash-cycle path, and a third of said assay resource stations is a read station including signal detection means and defining a read path;
   b) a first transfer station positioned adjacent a first end of the wash-cycle path for transferring a vessel from the incubation path to the wash-cycle path;
   c) a second transfer station positioned adjacent a second end of the wash-cycle path and a first end of the read path for selectively transferring a vessel from the wash-cycle path to either the incubation path or the read path; and
   d) analyzer control means comprising scheduling means for allocating assay resources to one of the reaction vessels as a function of an integral multiple of said time cycle and transfer control means for controlling the transfer of reaction vessels from one assay resource station to another according to a chronology selected from a plurality of different predetermined chronologies.

2. The analyzer of claim 1 wherein the incubation station includes an incubator belt that has an indexing time equal to the first indexing time.

3. The analyzer of claim 1 wherein the wash station has a second indexing cycle having a second indexing time and the wash transport means moves the reaction vessel along the wash-cycle path a fixed, distance during each second indexing cycle.

4. The analyzer of claim 3 wherein the first indexing time is an integral multiple of the second indexing time.

5. The analyzer of claim 4 wherein the first indexing time is three times as long as the second indexing time.

6. The analyzer of claim 1 wherein the first transfer station is positioned adjacent a second end of the read path, the first transfer station being adapted to transfer a vessel from the read path to the incubation path.

7. The analyzer of claim 1 wherein the incubation path intersects the wash-cycle path at at least two locations, the first transfer station being located at a first of the intersections and the second transfer station being located at a second of the intersections.

8. The analyzer of claim 1 wherein the track of the wash station includes a plurality of fingers extending upwardly from a floor.

9. The analyzer of claim 8 wherein the track of the wash station comprises a rigid metal wheel including said fingers and said floor.

10. The analyzer of claim 8 wherein the track of the incubation station comprises a plurality of fingers extending downwardly from a flexible belt.

11. The analyzer of claim 1 wherein the read station includes a movable track.

12. The analyzer of claim 11 wherein the track of the read station and the track of the wash station are joined as one endless track.

13. The analyzer of claim 12 wherein the endless track comprises a rigid wheel.

14. The analyzer of claim 13 wherein the wheel comprises a generally annular floor integrally formed with a plurality of fingers extending upwardly from the floor.

15. The analyzer of claim 14 wherein the fingers are spaced apart to define vessel-receiving recesses.

16. The analyzer of claim 12 wherein a generally vertical wall extends along opposed sides of the endless track.

17. The analyzer of claim 16 wherein each of the vertical walls have a pair of gaps formed therein, one gap of each of said pairs being associated with the first transfer station, the other gap of each of said pairs being associated with the second transfer station.

18. The analyzer of claim 17 wherein the incubation path extends through the gaps in the vertical walls at the first and second transfer stations.

19. An automated chemical analyzer for automatically analyzing a plurality of samples for at least two different analytes comprising:
   a) a plurality of assay resource stations each including an assay resource capable of performing a predetermined operation upon a sample-containing reaction vessel within a first indexing time, the first indexing time defining a time cycle of fixed duration, wherein:
      i) a first of said assay resource stations is an incubation station comprising movable transport having a plurality of fingers extending downwardly from a flexible belt and being adapted to carry a plurality of reaction vessels along an incubation path,
      ii) a second of said assay resource stations is a wash station including a movable track adapted to receive and carry a plurality of reaction vessels along a wash-cycle path, and
      iii) a third of said assay resource stations is a read station including signal detection means and a movable track adapted to received and carry a plurality of reaction vessels along a read path,
      iv) the track of the wash station and the track of the read station being joined in an endless track comprising a rigid wheel having a generally annular floor integrally formed with a plurality of fingers extending upwardly from the floor;
   b) a first transfer station located at a first intersection of the incubation path and the wash-cycle path at a positioned adjacent a first end of the wash cycle path and a second end of the read path, the first transfer station being adapted to transfer a vessel from the incubation path to the wash-cycle path or from the read path to the incubation path;
   c) a second transfer station located at a second intersection of the incubation path and the wash-cycle path adjacent a second end of the wash-cycle path and a first end of the read path for selectively transferring a vessel from the wash-cycle path to either the incubation path or the read path; and d) analyzer control means comprising scheduling means for allocating assay resources to one of the reaction vessels as a function of an integral multiple of said time cycle and transfer control means for controlling the transfer of reaction vessels from one assay resource station to another according to a chronology selected from a plurality of different predetermined chronologies for analyzing samples for the analyte.

20. An automated chemical analyzer for automatically analyzing a plurality of samples for at least two different analytes comprising:

a) a plurality of assay resource stations each including an assay resource capable of performing a predetermined operation upon a sample containing reaction vessel within a first indexing time, the first indexing time defining a time cycle of fixed duration, wherein a first of said assay resource stations is an incubation station comprising an elongated, movable transport means adapted to carry a plurality of reaction vessels along an incubation path, a second of said assay resource stations is a wash station including a movable transport means adapted to receive and carry a plurality of reaction vessels along a wash-cycle path, and a third of said assay resource stations is a read station including signal detection means;

b) a first transfer station means positioned adjacent a first end of the wash cycle path for transferring a vessel directly from the incubation path to the wash-cycle path;

c) a second transfer station means positioned adjacent a second end of the wash-cycle path and a first end of the read path for selectively transferring a vessel directly from the wash-cycle path to either the incubation path or the read path; and d) analyzer control means comprising scheduling means for allocating assay resources to one of the reaction vessels as a function of an integral multiple of said time cycle and transfer control means for controlling the transfer of reaction vessels directly from one assay resource station to another according to a chronology selected from a plurality of different predetermined chronologies for analyzing samples for the analyte.

\* \* \* \* \*